(12) United States Patent
Bate et al.

(10) Patent No.: US 7,176,027 B2
(45) Date of Patent: Feb. 13, 2007

(54) GENES AND REGULATORY DNA SEQUENCES ASSOCIATED WITH STRESS-RELATED GENE EXPRESSION IN PLANTS AND METHODS OF USING THE SAME

(75) Inventors: Nicholas J. Bate, Urbandale, IA (US); Timothy G. Helentjaris, Ankeny, IA (US); Xiping Niu, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 626 days.

(21) Appl. No.: 10/324,619

(22) Filed: Dec. 19, 2002

(65) Prior Publication Data

US 2003/0140381 A1 Jul. 24, 2003

Related U.S. Application Data

(60) Provisional application No. 60/343,034, filed on Dec. 20, 2001.

(51) Int. Cl.
*A01H 5/00* (2006.01)
*C12N 15/82* (2006.01)
*C12N 15/87* (2006.01)
*C12P 21/04* (2006.01)

(52) U.S. Cl. .................. 435/468; 435/320.1; 435/419; 800/281; 800/289; 536/23.6

(58) Field of Classification Search ................ 800/271, 800/278–280; 435/69.7, 320.1
See application file for complete search history.

(56) References Cited

U.S. PATENT DOCUMENTS 6,248,937 B1 * 6/2001 Finkelstein et al. ......... 800/290

FOREIGN PATENT DOCUMENTS

| WO | WO 99/41974 | 8/1999 |
| WO | WO 99/55840 | 11/1999 |
| WO | WO 00/46383 | 8/2000 |

OTHER PUBLICATIONS

Luscombe et al., Genome Biology, 1: 1-10, 2000.*
Finkelstein et al. , Plant Cell, 10: 1043-1054, 1998.*
Siberil et al., Eur. J. Biochem., 268:5655-5666, 2001.*
D'Aoust et al., Plant Cell, 11:2407-2418, 1999.*
Du et al., The Plant Journal, 24:837-847, 2000.*
Kasuga et al., Nature Biotechnology, 17;287-291, 1999.*
Arenas-Huertero, et al., "Analysis of Arabidopsis glucose insensitive mutants, gin5 and gin6, reveals a central role of the plant hormone ABA in the regulation of plant vegetative development by sugar", Genes & Development, 14:2085-2096, 2000.
Finkelstein, et al., "The *Arabidopsis abscisic* acid response locus ABI4 encodes an APETALA2 domain protein", The Plant Cell, vol. 10, 1043-1054, Jun. 1998.
Finkelstein, et al., "The *Arabidopsis abscisic* acid response locus ABI4 encodes an APETALA2 domain protein", The Plant Cell, vol. 10, 1043-1054, Jun. 1998, GenBank AF040959.
Huijser, et al., "The Arabidopsis sucrose uncoupled-6 gene is identical to abscisic acid insensitive-4; involvement of abscisic acid in sugar reponses", The Plant Journal, 23(5), 577-585, 2000.
Laby, et al., "The Arabidopsis sugar-insensitive mutants sis4 and sis5 are defective in abscisic acid synthesis and response", The Plant Journal, 23(5), 587-596, 2000.
Quesada, et al., "Genetic analysis of salt-tolerant mutants in *Arabidopsis thaliana*", GENETICS, 154: 421-436, Jan. 2000.
Rook, et al., "Impaired sucrose-induction mutants reveal the modulation of sugar-induced starch biosynthetic gene expression by abscisic acid signalling", The Plant Journal, 26(4), 421-433, 2001.
Soderman, et al., "Regulation and function of the arabidopsis ABA-insensitive4 gene in seed and abscisic acid response signaling networks", Plant Physiology, vol. 124, 1752-1765, Dec. 2000.
Finkelstein, et al., "The arabidopsis abscisic acid response gene ABI5 encodes a basic leucine zipper transcription factor", The Plant Cell, vol. 12, pp. 599-609, Apr. 2000.
Finkelstein, "Mutations at two new arabidopsis ABA response loci are similar to the abi3 mutations", The Plant Journal, 5(6), pp. 765-771, 1994.
Nakamura, et al., "Physical interactions between ABA response loci of arabidopsis", The Plant Journal, 26(6), pp. 627-635, 2001.
Signora, et al., "ABA plays a central role in mediating the regulatory effects of nitrate on root branching in arabidopsis", The Plant Journal, 18(6), pp. 655-662, 2001.

* cited by examiner

*Primary Examiner*—Ashwin Mehta
*Assistant Examiner*—Vinod Kumar
(74) *Attorney, Agent, or Firm*—Pioneer Hi-Bred International

(57) ABSTRACT

Compositions and methods for modulating gene expression in plants are provided. The compositions comprise novel genes and promoters as well as regulatory and binding elements therein. The methods comprise the modulation of gene expression using the compositions of the invention. Compositions and methods are provided to reduce the impact on plants of biotic and abiotic environmental stresses. Accordingly, the compositions and methods may also be used to decrease the necessary amounts of conventional stress reduction treatment as well as to increase plant yield.

17 Claims, 9 Drawing Sheets

Figure 1

```
   1 CTGCAAGCGTGCGGGCCACGTGGCATGAGGTTTAAGTGGGCCAGGCAAAGGAGAAATCAGCCCATTTGCACCTCTTTCCATCCCCTTTTTCTATTTTCTA
 101 TTTTAATTTCCTATTTCAATTCTATGTTCCAAATCAAATCTAGTTTTTAATTTCAAATTCAAGTTTAATGCACAAACAATAACTCCAGCATGGGATGCAA
 201 CAAATTTATATCTATATATATTTATATTGTTGTTAATCTATTCATTCAAGTAAATGCATCAAAATGCACACACACAAAATATATGTATTTTAAGAAAGAT
 301 AATTTCTAGTTAAGAGAACAATTTAGAAATATATGATTTGTCAAAGGAATAACTAAATTCTTATAGAGATCATTTTTATTTACCCTTTTATTAGAAAACA
 401 TTATTGTTTTAGGAAAAGTAGTTCCAAAGCTAAGACAATTCTTATGGGAAATATATTTTAATTCAAAATCTTGGAGAATTTCACTAAACTTTCAAAATAA
 501 GATTTTTGGGTGTTACAAATGCCCCATTGACTAGGAGGGACTTAAGAGTCCAAGAGAGATCTATAGGTCATAAGGGCCTCAAGATCCGGTCTCCTAACAT
 601 GGAGGGTGTGGCAGAGAGAGTAGGAGAGCCTCGGTGGCAAACATAGTCCTAGTGGTCCTAGGAGCCCTAGGATCTAGTCCCCTCGCATGGAGAGTGGTGG
 701 AGACATAGGTGAGCCCTAGGGGCGGAGAGGCCCTCGGGATTTGGTCTCCTGAAATGGAGGGCCTAGACTTAGTTGGAGTCGAGCATGGTCCCCTAGGGTGT
 801 GGAGCCCCTAGTCATATGACTAGCATCGATTGAACCTTTTTTTGAGTTTTCTTCTATCAAATAGATCTTCCATAGGCATATTACCGATATCCAAAGATAT
 901 GACATCCTCTTGACGTAAATAGTAGCCATTACATATGTTTGATCTAACTTGATTGTATATTATTGGCAAAACAATGTATAAGCTCTAGTAGCTATTCATT
1001 ATTTGGCCACACTAAGATTTTCATAAAAAAATAAAAAATTGTAAAGTTTAGTTACAACTAGTTAAATTATGTTCACATATCCTCATGTCTTCTTTACTTT
1101 TCAATGTGCCCTTGTCCTCGTGTTAGGGGCGCATACACAGTTATTTTGCATGCAACGATAATATATATACAGTTTAAATGCAACGGCGTAACAAGGTAA
1201 TATTCCACTAGAATGTACATACGCGTTTGCTAGCGTATATGTATATATTATAAGATGATTTCAATGGATTGTCACGACATTTCATGAGTTAAGTGTGGTG
1301 TTCGTAAAGAAGACATATGATATGCAAGGTGAAACTTTCATAAGTAAAAGAAAATTTCTAATATTTATGTTGGTCAACCTTTCGTATGTTTAACTAGGTC
1401 GTTTATGGAAAATATTATAACTTTTGTATATCTCAAAATAACTTTATTTATGGAAATAAATTTTAAAATTGATGTAATTATACTGATTATATACTTAAATA
1501 TTAATATCTTTGTATATTTAATCAAAGTTAAAGGAAATGGTACTTAGTTTTTTTTAAAAAAAGCGAAGGATTAATCGATTCGCGAGAACATTTATATATG
1601 ACTGTTGACATGCCAAGCAGGAGGGCTTTGCTTCTCACATCCGATGATATCACTGGGAAATGGAGTTGACCGGTGCGTGCAGTAGTCATTTCCAAGAAGC
1701 TTTTAACCAAGTTGGTGACAGGTAGACACGAAGGAAGCCGCGTAGGAGTAATCCTAGTACAGTAGTACTACGTAGTAAAAATCTGTTGGACGATCGATCC
1801 AAGTGAAGCAGTGCATCAAAGAACGCTGCACACATCGATCTCGATCCTGTCCCTGCATGCATGCACGCACCGAGCAACGAAGCGCTGCACACAATGACAC
1901 AAGCCAGTAAGTCAGAAGTCGATTGCTCCATCAACCGTATACTAGCTTAATTCCGCAATGACTCCGATGATCTACATGCTGGATTCCGCAATGACTCCGA
2001 TGATCTACAGCATGCATGGCACACTCCCCCGGCCTCTACCACACCAACCAACAAGAATCTGGCTTTTTAAACTAGGTGAGAAAGATTCAAACACACCCGT
2101 TTTTATACGTTTTTGCAAAATTCTGAAAAAACTAGAAAACTGTTGATAGTAATTTTTGCCAGTTTCTCATAATCCAAAAAGAAACAAATAAAATCATTTA
2201 CTGACACCCGAATACTGTATCAATTCTGGCTCGGAATCTACTAGATTTTATAGAAATTACAGACAAAAACTCTCTTTTTTTAATTCCGAAACTGATCTAA
2301 AGCTGCTCGCTGTACTGCACTATGCACTCTCTCACCTCCCTTTATATTTGACCACCGCCCCTCTCCACCAAGCGCATCCACCTCGACCTCCATCCCTAGC
2401 GCTCTCGCCCCAAAGCACGCCGCAGGCGCAGAGCCATCACCACCATCCTTCCCCCCCCTCTATCTCTCTCTACCCCATCCCTCCTCTCTCTCCTCATATA
2501 CCAGCGACGCTGCCTCCTTCCATGGAAGCCAGCAACAATGAGTCCGCGCCCACGGCCGAGGCAGCTGCAGGCAGCGGCCCGGCCGGCGGAGAAGGGCGGA
            M   E   A   S   N   N   E   S   A   P   T   A   E   A   A   A   G   S   G   P   A   G   G   E   G   R       26
2601 AGGGCAAGGCGCCCAAGGGCGGGCCCGAGAACGGCAAGTTCCGGTACCGCGGCGTGCGGCAGCGGAGCTGGGGCAAGTGGGTGGCGGAGATCCGCGAGCC
         K   G   K   A   P   K   G   G   P   E   N   G   K   F   R   Y   R   G   V   R   Q   R   S   W   G   K   W   V   A   E   I   R   E   P       60
2701 GCGGAAGCGCTCCCGCAAGTGGCTCGGCACCTTCGCCACCGCCGAGGACGCCGCGCGCTACGACCGCGCGCTCCTCCTCTACGGCCCCCGCGCG
         R   K   R   S   R   K   W   L   G   T   F   A   T   A   E   D   A   A   R   A   Y   D   R   A   A   L   L   L   Y   G   P   R   A       93
2801 CACCTCAACCTCACCTCCCCGCCGCCTCCTACGCTCGCCGCCGCCGCGCTCGCACCCGCACTCCTCCGCCACGTCGTCTGCCCCGCCAGCGCTCCGCCCGC
         H   L   N   L   T   S   P   P   P   P   T   L   A   A   P   R   S   H   P   H   S   S   A   T   S   S   A   P   P   A   L   R   P       126
2901 TCCTGCCGCGCCCGCCACTGCACCAGCTCTCCAGCGACGGTGCTCCTGCACCGGATTTCCACTACCACAACCAGTTCCAGCGCCGTCTCTTGCCGCAGCC
         L   L   P   R   P   P   L   H   Q   L   S   S   D   G   A   P   A   P   D   F   H   Y   H   N   Q   F   Q   R   R   L   L   P   Q       160
3001 GACACCCCACACTATACTACGCCAACACGGCCACGGCGTCCACAGTGACCACCAGTGTGCCGACACGGGTGGCGGTTCCGCAGGAGCCGGCCATCGCGCCC
         T   P   T   L   Y   Y   A   N   T   A   T   A   S   T   V   T   T   S   V   P   T   R   V   A   V   P   Q   E   P   A   I   A   P       193
3101 GCAGTAGGCTCCTCGACGTCACTACAGGAGCCGCAGGTAGGTACGCCGGAGGAGGCGCGCGGGGAGGCAGGGTGGGACTACAACGGCGGCGAGGAGGAGG
         A   V   G   S   S   T   S   L   Q   E   P   Q   V   G   T   P   E   E   A   R   G   E   A   G   W   D   Y   N   G   G   E   E   E       226
3201 ATTATGCGGCGGCGCTGCTGTGGGACGAGCCGGAGCCCTTCTTCTGGTTTGATGTCTTCCTCAAGTGATGGCCAGCGCACGACGCTGCATGCCAACTCGA
         D   Y   A   A   A   L   L   W   D   E   P   E   P   F   F   W   F   D   V   F   L   K   *                                                     248
3301 ATCCTGCATGGTTGGTTTGGAGTTTCGGAGTGACGGCAGCTCATGCTCATGCATCTGCATGCATGTGTTGGGCAAGTAAGCAAGCAAGAAAGGTAGATAG
3401 GCTTGCTAGCTAGGGTTTCTGATTCCTTTGTACTAAATTATCTTTATATTTTTTTATCTTATCCTTCTTTTTTCCCTAAGGGTGTGATTGAGGTATAGT
3501 AATGTTAGGTGGTATTACTGGTGGGAGGATTTAGGGGTTCTTTGTTGATTTAAAGATTCAATTTTGAATCACATCGAATCGATTTCTTGCATGGGGATGCA
3601 ATCTATTTAATTGTGGCATGTATAAAAATCAGCGATGCAACAAAAAAAAAAAAAAAAAAAAAAAAAAA
```

```
Zm ABI4     (1)   ------------MEASNN--ESAPTAEAAAGSGPAGGEGRKGKAPKGGP
At ABI4     (1)   MDPLASQHQHNHLEDNNQTLTHNNPQSDSTTDSSTSSAQ-RKRKG-KGGP
Consensus   (1)                D  N      P ADA    S  A A   RK KA KGGP
                  51                                               100
Zm ABI4     (36)  ENGKFRYRGVRQRSWGKWVAEIREPRKRSRKWLGTFATAEDAARAYDRAA
At ABI4     (49)  DNSKFRYRGVRQRSWGKWVAEIREPRKRTRKWLGTFATAEDAARAYDRAA
Consensus   (51)  DN KFRYRGVRQRSWGKWVAEIREPRKRSRKWLGTFATAEDAARAYDRAA
                  101                                              150
Zm ABI4     (86)  LLLYGPRAHLNLTSPPPPTLAAPRS----HPHSSATSSAPPALRPLLPRP
At ABI4     (99)  VYLYGSRAQLNLTPSSPSSVSSSSSSVSAASSPSTSSSSTQTLRPLLPRP
Consensus   (101)  L LYG RA LNLT  P SLAA  S         S SSSA   LRPLLPRP
                  151                                              200
Zm ABI4    (132)  PLHQLSS------DG--AP-----------APDFHYHNQFQRR------
At ABI4    (149)  AAATVGGGANFGPYGIPFNNNIFLNGGTSMLCPSYGFFPQQQQQQNQMVQ
Consensus  (151)        L       G                   P FF   Q Q
                  201                                              250
Zm ABI4    (156)  ---LLPQPTPTLYYAN---------TATASTVTTSVPTRVAVPQEP---
At ABI4    (199)  MGQFQHQQYQNLHSNTNNNKISDIELTDVPVTNSTSFHHEVALGQEQGGS
Consensus  (201)         Q  LH            T     T STS     VAL QE
                  251                                              300
Zm ABI4    (190)  -----------AIAPAVGSSTSLQEP-----------QVGTPEEARGE
At ABI4    (249)  GCNNNSSMEDLNSLAGSVGSSLSITHPPPLVDPVCSMGLDPGYMVGDSS
Consensus  (251)             AIA AVGSS SI  P             G
                  301                              333
Zm ABI4    (216)  AGWDYNGGEEEDYAAALLWDEPEPFFWFDVFLK
At ABI4    (299)  TIWPFGGEEEYSHNWGSIWDFIDPILGEFY---
Consensus  (301)    W F G EE   H  A IWD DP
```

B

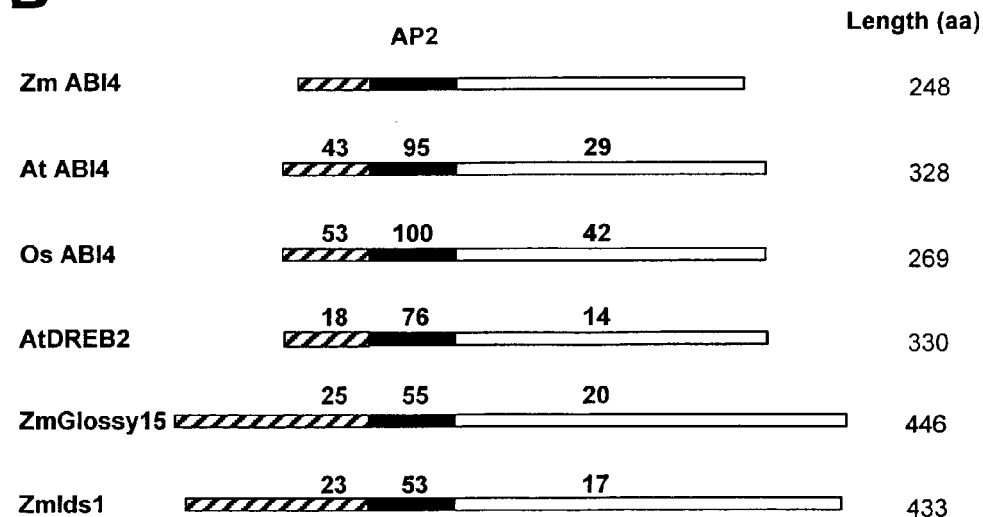

Figure 3
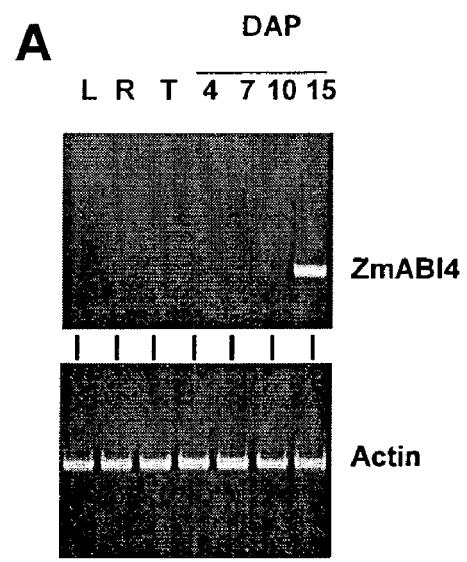
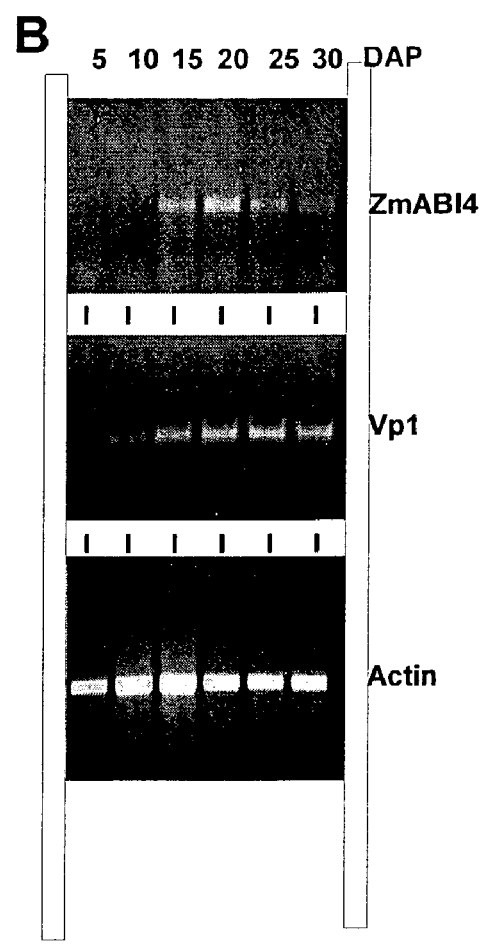

FIGURE 4

|  | Left Primer | Selected Sequences | Right Primer | Gene |
|---|---|---|---|---|
| Group I | | | | |
| 34 | CAGCTGAATTCGTAGGAC | CACCGCCCCT | GAACGGATCCAGATCTCA | ZmABI4 |
| 17 | CAGCTGAATTCGTAGGAC | CACCGCCCCC | GAACGGATCCAGATCTCA | |
| 38 | CAGCTGAATTCGTAGGA | CACCGCCCCC | CGAACGGATCCAGATCTCA | |
| 13 | CAGCTGAATTCGTAGGACA | CACCGCCCCG | AACGGATCCAGATCTCA | |
| 79 | CAGCTGAATTCGTAGGACA | CACCGCCCCG | AACGGATCCAGATCTCA | |
| 65 | CAGCTGAATTCGTAGGAC | CACCGCCCCA | GAACGGATCCAGATCTCA | |
| 22 | CAGCTGAATTCGTAGGA | CACCGCCGCC | CGAACGGATCCAGATCT | |
| 24 | CAGCTGAATTCGTAGGA | CACCGCCGCC | CGAACGGATCCAGATCTCA | |
| 31 | CAGCTGAATTCGTAGGAC | CACCGCCGCC | CGAACGGATCCAGATCTCA | |
| 28 | CAGCTGAATTCGTAGGA | CACCGCCGCC | CGAACGGATCCAGATCTCA | |
| 4 | CAGCTGAATTCGTAGGA | CACCGCCACC | CGAACGGATCCAGATCTCA | |
| 61 | CAGCTGAATTCGTAGGA | CACCGCCCGT | CGAACGGATCCAGATCTCA | |
| 8 | CAGCTGAATTCGTAGGACA | CGCCGCCCCG | AACGGATCCAGATCTCA | |
| 42 | CAGCTGAATTCGTAGGACAGC | GCCGCCCGA | ACGGATCCAGATCTCA | |
| 1 | CAGCTGAATTCGTAGGA | CGCCGCCGT | TGAACGGATCCAGATCTCA | |
| 73 | CAGCTGAATTCGTAGGAC | CGCCGCCAT | GAACGGATCCAGATCTCA | |
| 3 | CAGCTGAATTCGTAGGACC | CGCCGCCTG | AACGGATCCAGATCTCA | |
| 60 | CAGCTGAATTCGTAGGACT | CGCCGCCTG | AACGGATCCAGATCTCA | |
| 71 | CAGCTGAATTCGTAGGACGGC | GCCGCATGA | ACGGATCCAGATCTCA | |
| 74 | CAGCTGAATTCGTAGGACGGC | GCCACCGAA | CGGATCCAGATCTCA | Rab17 |
| 20 | CAGCTGAATTCGTAGGACG | TGCCGCCCG | AACGGATCCAGATCTCA | |
| Group II | | | | |
| 5 | CAGCTGAATTCGTAGGA | CGGTGCGTGT | TGAACGGATCCAGATCTCA | |
| 50 | CAGCTGAATTCGTAGGA | CGGTGCGCTG | TGAACGGATCCAGATCTCA | |
| 9 | CAGCTGAATTCGTAGGA | CGGTGCGCAC | CGAACGGATCCAGATCTCA | |
| 63 | CAGCTGAATTCGTAGGA | CGGTGCGGGT | TGAACGGATCCAGATCTCA | |
| 37 | CAGCTGAATTCGTAGGA | CGGTGCACCC | TGAACGGATCCAGATCTCA | |
| 51 | CAGCTGAATTCGTAGGA | CGGTGCACTC | CGAACGGATCCAGATCTCA | |
| 48 | CAGCTGAATTCGTAGGA | CGGTGCAGCC | CGAACGGATCCAGATCTCA | |
| 25 | CAGCTGAATTCGTAGGA | CGGTGCCCCC | CGAACGGATCCAGATCTCA | |
| 64 | CAGCTGAATTCGTAGGA | CGGTGCCTCC | CGAACGGATCCAGATCTCA | |
| 35 | CAGCTGAATTCGTAGGA | CGGTGCCTTG | TGAACGGATCCAGATCTCA | |
| 41 | CAGCTGAATTCGTAGGA | CGGTGCCTCT | CGAACGGATCCAGATCTCA | |
| 53 | CAGCTGAATTCGTAGGA | CGGTGCCACT | CGAACGGATCCAGATCTCA | |
| 6 | CAGCTGAATTCGTAGGA | CGGTGCTCCC | TGAACGGATCCAGATCTCA | |
| 7 | CAGCTGAATTCGTAGGA | CGGTGCTCCC | CGAACGGATCCAGATCTCA | |
| 69 | CAGCTGAATTCGTAGGA | CGGTGCTCCC | CGAACGGATCCAGATCTCA | |
| 19 | CAGCTGAATTCGTAGGA | CGGTGCTCCT | TGAACGGATCCAGATCTCA | |
| 46 | CAGCTGAATTCGTAGGA | CGGTGCTCTT | TGAACGGATCCAGATCTCA | |
| 14 | CAGCTGAATTCGTAGGA | CGGTGCTGCC | CGAACGGATCCAGATCTCA | |
| 32 | CAGCTGAATTCGTAGGA | CGGTGCTGCC | CGAACGGATCCAGATCTCA | |
| 55 | CAGCTGAATTCGTAGGA | CGGTGCTTTC | CGAACGGATCCAGATCTCA | |
| 26 | CAGCTGAATTCGTAGGA | CGGTGCTTTC | CGAACGGATCCAGATCTCA | |
| 76 | CAGCTGAATTCGTAGGA | CGGTGCTTCC | CGAACGGATCCAGATCTCA | |
| 77 | CAGCTGAATTCGTAGGA | CGGTGCTTCC | CGAACGGATCCAGATCTCA | |
| 80 | CAGCTGAATTCGTAGGA | CGGTGCCGCC | CGAACGGATCCAGATCTCA | |
| 68 | CAGCTGAATTCGTAGGA | CGGTGCATCC | CGAACGGATCCAGATCTCA | |
| 56 | CAGCTGAATTCGTAGGA | CGGTGGCGGT | CGAACGGATCCAGATCTCA | HVA22 |
| 23 | CAGCTGAATTCGTAGGA | CGGTGGCTTT | CGAACGGATCCAGATCTCA | |
| 59 | CAGCTGAATTCGTAGGA | CGGTGGGGCT | AGAACGGATCCAGATCTCA | |
| 62 | CAGCTGAATTCGTAGGA | CGGCGCCTTC | TGAACGGATCCAGATCTCA | |
| 75 | CAGCTGAATTCGTAGGA | CGGCGCCACC | CGAACGGATCCAGATCTCA | |
| 29 | CAGCTGAATTCGTAGGA | CGGCGCGGTC | TGAACGGATCCAGATCTCA | |

Rev-comp for group II     3'GCCAC 5'

Consensus     5'CACCG 3'

```
1) Maize ABI4      -67 TTTGAC CACCGC CCCTCT -50
2) Mutated ABI4-1          G
3) Mutated ABI4-2           T
4) Mutated ABI4-3              C
5) Mutated ABI4-4               G
6) Maize Rab 28    -242 TGGGCA TGCCGC CGCGAC -225
7) Barley HVA1      -81 TACGAG CACCGC CGCGCA  -64
8) Barley HVA22     -70 TGCCAT TGCCAC CGGCCC  -53
9) Maize Rab17     -195 CCGGGC CACCGA CGCACG -178
10)Rice Rab16B     -238 TGGCAC CACCGA CACGGC -221
11)CdeT27          -125 AATAAT CACCGA CTTTCA -108
```

B

```
AtABI4    AAG TATAAATAAAAGAAG CACCGCCC TAA
ZmABI4    CTT TATATTT----GA-C CACCGCCC CTC
OsABI4    CTT TATATTT----GA-C CACCGCCC CTC
```

C

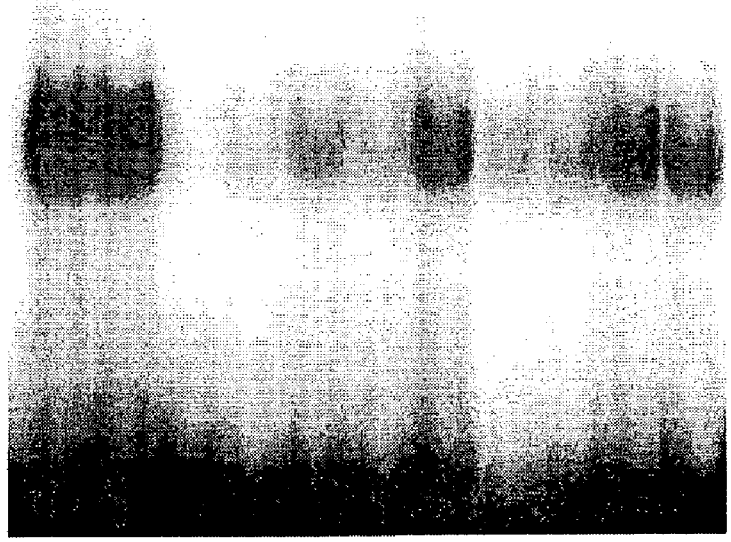

A

B

|  | CE/DRE |
|---|---|
| ADH1 | -339 CACCGA -334 |
| Em1 | -114 CGCCGC -109 |
| Em6 | -216 CGCCGC -211 |
|  | -239 CGCCGC -234 |
| ApL3 | -574 CACCGA -579 |
| PC | -708 TACCGA -703 |
|  | -748 TACCGA -743 |

A

B

```
AtABI4    AAG TATA AATAAAAGAAG CACCGCCC TAA
ZmABI4    CTT TATA TTT----GA-C CACCGCCC CTC
```

Figure 8
A
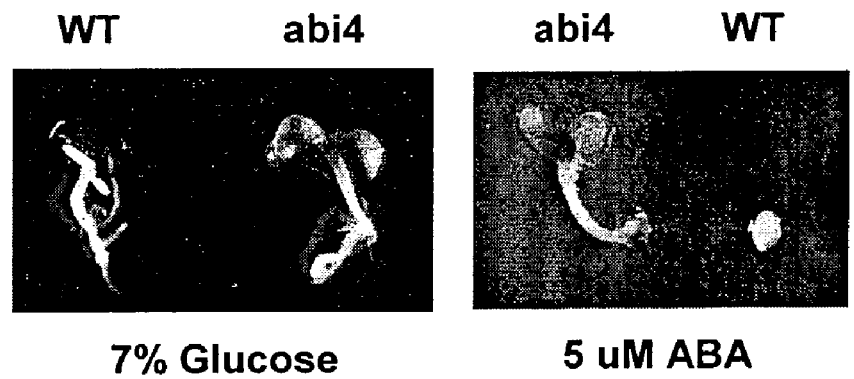
7% Glucose        5 uM ABA
B
Cotyledon expansion ■
Green primary leaves ▦
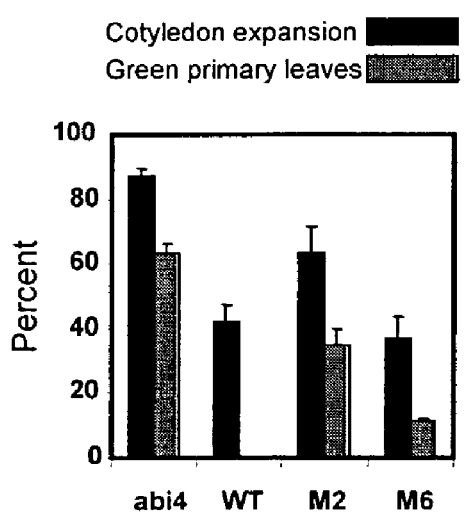
C
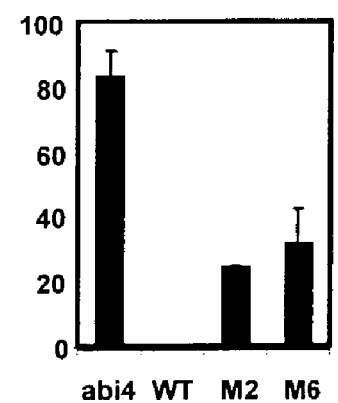
D
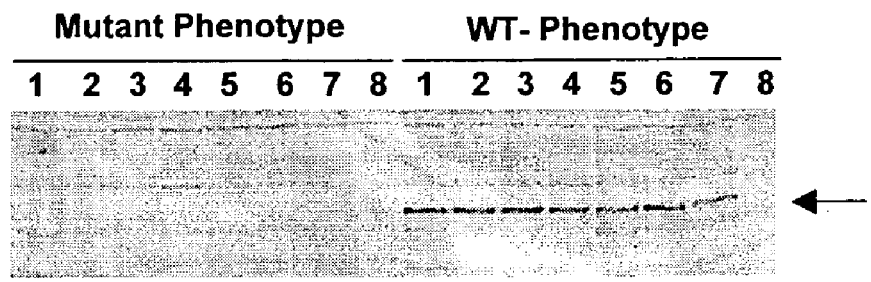

GENES AND REGULATORY DNA SEQUENCES ASSOCIATED WITH STRESS-RELATED GENE EXPRESSION IN PLANTS AND METHODS OF USING THE SAME

This application claims priority to, and hereby incorporates by reference, U.S. provisional application No. 60/343,034, filed Dec. 20, 2001.

FIELD OF THE INVENTION

The invention relates to nucleotide sequences and proteins related to stress in plants, particularly the genetic manipulation of plants in order to enhance crop yield and disease resistance. Improvements in stress tolerance are also provided.

BACKGROUND OF THE INVENTION

Agricultural yields have historically been threatened and often destroyed by extremes of temperature as well as by drought and flood. With the changes in environment attributed to global warming, extreme weather conditions are expected to increase. Agricultural yields are also threatened in many important agricultural areas due in part to long-term effects of farming practices on the land. For example, in many areas, the chemical composition of the soil has actually been altered by the accumulation of salts such that increased salinity is now a hindrance to optimal plant growth. See Boyer (1982) *Science* 218: 443–448. Other stresses of economic importance to agriculture include those imposed by pathogens as well as nitrogen starvation, ozone, and increased concentrations of heavy metals in the soil.

Stress responses in plants and ways of improving stress responses have been widely studied. Many links have been discovered between stress responses generally and pathogen attack, so approaches to improving stress responses often have a positive impact on plant resistance to pathogens. See Farmer (2000) *Genome Biol.* 1(2): reviews 1012.1–1012.3. For example, in *Arabidopsis*, the response to ozone involves the same salicylic acid-dependent pathway that is involved in microbial pathogen resistance. See Sharma and Davis (1997) *Free Radic. Biol. Med.* 23(3): 480–88.

Salt tolerance in plants has also been widely studied. One approach to improving salt tolerance is alteration of the metabolic responses of crop plants. Most genes that show increases in activity or amount in response to high salt concentration also are induced by abscisic acid ("ABA"), and it has also been shown that many stress-inducible genes in plants, for example, oxalate oxidase, are also induced in the normal course of development.

Because plants are subject to a number of environmental stresses, regulation of expression of helpful gene products in response to stress may decrease damage resulting from such environmental stresses and improve crop performance and yields. Conventional plant breeding has improved yields for many crops grown under stressful conditions. However, continued efforts to improve plant response to stress has led many to the conclusion that further improvements will come not from conventional plant breeding but rather from the more precisely focused changes made possible by genetic engineering. See Smirnoff and Bryant (1999) *Nature Biotechnol.* 17: 229; Ceccarelli and Grando (1996) *Plant Growth Reg.* 20: 149–155.

Experiments in improving plant stress tolerance have shown some success. For example, constitutive overexpression of DREB1A, a stress-regulatable transcription factor from *Arabidopsis*, conferred an improved response to stresses including dehydration, freezing, and increased salinity. Kasuga et al. (1999) *Nature Biotechnol.* 17, 287–291. However, there was a significant drawback of the constitutive expression of the transgene: under normal growth conditions (i.e., without stress), plant growth was severely impaired. Fortunately, when the transgene was expressed only in response to stresses such as cold and water stress, the plants exhibited stress tolerance without the growth impairment resulting from constitutive expression. Thus, appropriate expression of helpful transgenes has potential for the improvement of stress tolerance of crops. Accordingly, there is a need for transgenes which can improve plant response to stress as well as a need for mechanisms to appropriately express these transgenes.

On the other hand, expression of certain genes known to be related to stress tolerance may improve plant growth and yield even in the absence of stress. For example, altering the ABA and sugar signaling of a plant may improve yield under non-stress conditions. Thus, there is a need for controlled and targeted manipulation of stress-related gene expression for improved performance of plants in the absence of stress.

Stress-inducible genes of plants play an important role in other aspects of plant growth, development, and defense mechanisms, as suggested by their complex patterns of regulation and roles in response to stress. See, e.g., Berna and Bernier (1999) *Plant Mol. Biol.* 39(3): 539–549; Roitsch (1999) *Curr. Opin. Plant Biol.* 2(3): 198–206. For example, wheat oxalate oxidase causes release of hydrogen peroxide in the apoplast in response to stress as well as during normal development. Other stress response genes also play a role in non-stress physiological processes, such as berry ripening. Davies and Robinson (2000) *Plant Physiol.* 122(3): 803–812. The fact that stress-response genes play roles in many other physiological processes highlights the importance of a narrowly tailored genetic alteration in improving stress response.

Stress responses in plants often include dramatically increased expression of sets of genes. However, stress responses in plants are not exclusively a matter of increased gene expression, but can be more complex. For example, studies of potato show that wounding of the potato tissue led to increased gene expression which resulted in tissue repair. In contrast, in potato subjected to impact injury and loss of membrane integrity, the enzyme polyphenol oxidase is redistributed at the subcellular level. See Partington et al. (1999) *Planta* 207(3): 449–460.

Abscisic acid ("ABA") is a plant hormone important in modulating the response of plants to stresses such as drought, salt, and cold stress. ABA is also important in many aspects of plant metabolism and development, including seed development, response of tissues to sugar signals (Rook et al. (2001) *Plant J.* 26: 421–433), seed dormancy, seed desiccation tolerance, storage of seed proteins and lipids, and stomatal movement. See Merlot and Giraudat (1997) *Plant Physiol.* 114: 751–757. Studies of the relationship between ABA and plant responses to sugar have revealed similar responses of plants to both signals, and that both ABA and sugar play a role in germination, photosynthesis, and development. See Huijser et al. (2000) *Plant J.* 23: 577–585; Arenas-Huertero et al. (2000) *Genes Dev.* 14: 2085–2096; Laby et al. (2000) *Plant J.* 23: 587–596.

A handful of genes important to the response of plants to ABA have been cloned, including genes which encode transcriptional regulators from maize (the Viviparous1 gene, or Vp1). The *Arabidopsis* ABI4 gene also appears to be a transcriptional regulator and is thought to play a general role in ABA response. See Finkelstein et al. (1998) *Plant Cell* 10: 1043–1054 (1998); Arenas-Huertero et al (2000) *Genes Dev.* 14: 2085–2096. Other ABA-response genes have been identified as protein phosphatase 2C genes and a farnesyl transferase gene. See Finkelstein et al. (1998) *Plant Cell* 10: 1043–1054.

Mutations in ABI4 have been isolated in screens for mutations showing: increased salt tolerance (Quesada et al. (2000) *Genetics* 154: 421–436); seed germination in the presence of high levels of ABA; seed germination in the presence of high salinity (Quesada et al. (2000) *Genetics* 154: 421–436); and seed germination in the presence of high levels of glucose (Huijser et al. (2000) *Plant J.* 23: 577–585, and references cited therein). Thus, ABA-insensitive mutants have defects in dormancy of seed. In addition, ABI4 mutant plants have altered seed protein composition. These defects are consistent with the proposed roles for ABI4 in seed development such as regulating seed responses to ABA. See Finkelstein et al. (1998) *Plant Cell* 10: 1043–1054; Soderman et al. (2000) *Plant Phys.* 124: 1752–1765. However, expression analysis of *Arabidopsis* has showed that AtABI4 expression is not limited to seed.

*Arabidopsis* plants which contain mutations in the ABI4 gene are typically insensitive to ABA and show defects in stress responses, including those involving root growth, stomatal regulation, and regulation of stress-induced genes. ABI4 mutants have been isolated in screens for plant mutants causing a defect in feedback inhibition of photosynthesis and induction of storage processes which normally result in the presence of high levels of sugar. See Rook et al. (2001) *Plant J.* 26: 421–433. ABI4 mutants in *Arabidopsis* have also been identified as insensitive to certain sugars, indicating that ABI4 plays a role in a sugar-response pathway that contributes to regulation of photosynthesis. See Huijser et al. (2000) *Plant J.* 23: 577–585.

The *Arabidopsis* ABI4 gene has been cloned and sequenced. See Finkelstein et al. (1998) *Plant Cell* 10: 1043–1054. The predicted protein product of the ABI4 gene shows homology to plant transcriptional regulators which contain the conserved APETALA2 DNA-binding domain. However, outside this conserved region, the *Arabidopsis* ABI4 gene shared a much lower degree of identity with these other APETALA2 genes (around 40%; see Finkelstein et al. (1998) *Plant Cell* 10: 1043–1054). The null alleles of ABI4 isolated in screens for salt-tolerant mutants of *Arabidopsis* were shown to be missing the APETALA2 DNA binding domain.

Other motifs important to stress responses include a motif called DREB/CBF. See Smirnoff and Bryant (1999) *Nature Biotechnol.* 17: 229. Some genes important to stress response to freezing and water stress have been shown to contain the DREB/CBF motif. See Close (1997) *Physiol Planta* 100: 291–296. Similarly, studies have led to the discovery of cis-acting regulatory sequences important in the stress response, such as ABA response elements (Shen and Ho (1995) *Plant Cell* 7(3): 295–307) and the C-repeat/dehydration responsive element (DRE). See Stockinger et al. (1997) *Proc. Natl. Acad. Sci. USA* 94: 1035–1040. In *Arabidopsis*, Stockinger et al. isolated a CBF1 protein which binds to the DRE and thereby stimulates transcription in response to water stress and low temperatures. CBF1 also contains an APETALA2 domain. Stockinger et al. (1997) *Proc. Natl. Acad. Sci. USA* 94: 1035–1040.

Nevertheless, water stress around the time of flowering has a significant negative impact on maize yield. One potential strategy to reduce these effects is to engineer the maize plant to improve the stress response. Previously characterized regulatory sequences are present in only a subset of response genes. Thus, there is a need in the area for the tools to create such improvements, including suitable combinations of promoters, response elements, and transcription factors to appropriately control expression of helpful genes.

SUMMARY OF THE INVENTION

Compositions and methods for improving the response of a plant to an environmental stress are provided. The compositions comprise novel sequences, including the maize ZmABI4 gene and its native promoter. The protein product of the native gene binds to recognition sequences and thereby provides a means for modulation of transcription of genes operably linked to the recognition sequence. The full-length promoter provided contains such a recognition sequence and thus can provide modulation of expression of an operably linked coding region. The sequences provided may also be used in part and may also be used in combination with other sequences to provide the desired regulation of gene expression. Methods of the invention utilize the novel sequences of the invention to genetically modify the genome of an organism.

Thus, the promoter of the invention can be used to drive transcription of any coding region of interest. The promoter may be used in whole or in part, or in combination with other promoters in whole or in part, to achieve desired patterns of transcription and expression. In some embodiments, very short sequences of the promoter are used in synthetic promoter constructs to confer desired patterns of transcription and expression of a gene operably linked to the synthetic promoter construct. For example, elements of the provided promoter may be used in a synthetic promoter construct to provide induction of transcription in response to cold stress or drought stress.

The invention also provides a coding region which encodes the ZmABI4 protein. This coding region may be provided in an integration vector or an expression vector in combination with various promoter constructs to achieve expression of the coding region in a suitable host plant. In this manner, the invention provides the ZmABI4 protein, a transcription factor which may be used to improve the stress response and yield of crop plants. For example, overexpression of the ZmABI4 protein may activate one or more effector genes, enabling the plant to respond to stress more rapidly or to a greater extent or may alter the composition of seeds. Alternatively, antisense constructs may be provided to interfere with translation of the ZmABI4 protein, modulating the plant response to stress conditions.

In some embodiments of the invention, a nucleotide sequence encoding the ZmABI4 protein is placed in operable linkage with a stress-inducible promoter and stably integrated into the genome of a suitable host such as maize. Other embodiments include the operable linkage of ZmABI4 with developmentally controlled promoters to alter the protein, oil or carbohydrate composition of the host plant.

In other embodiments of the invention, a nucleotide sequence encoding the ZmABI4 protein is placed in operable linkage with a chemically-inducible promoter and stably integrated into the genome of a suitable host such as maize. In these embodiments, maize plants which have been subjected to stress may be treated with the appropriate chemical in order to induce expression of the ZmABI4 protein, thereby ameliorating the effect of the stress on the maize and improving crop yield. Induction of ZmABI4 might also provide protection against pathogen attack which often is associated with increased stress.

The invention also provides a binding site for the ZmABI4 protein. In certain embodiments of the invention, a promoter may be modified to include said binding site such that expression of a coding sequence, operably linked to the modified promoter, is induced by the ZmABI4 protein. Said target gene may be endogenous or exogenous to the modified plant, and the promoter may be native or heterologous to the coding sequence.

BRIEF DESCRIPTION OF THE DRAWINGS

FIG. 1 shows the nucleotide and deduced amino acid sequences of the ZmABI4 gene, including the upstream region. This nucleotide sequence is also included in the Sequence Listing as SEQ ID NO: 5. The coding sequence and corresponding amino acids are also included in the Sequence Listing as SEQ ID NO: 2.

FIG. 2, Panel A, shows a protein sequence comparison of *Zea mays* protein ZmABI4 with *Arabidopsis thaliana* protein ABI4 (AtABI4, GenBank accession number AF040959). Single-letter amino acid residues of AtABI4 and ZmABI4 are aligned and the consensus sequence is presented underneath. The conserved AP2 domain is boxed.

FIG. 2, Panel B, shows a schematic diagram comparing the ZmABI4 protein sequence with other AP2-domain-containing proteins. The predicted ZmABI4 protein is aligned with AtABI4, OsABI4 (contigs 4094 and 1079; draft rice sequence), AtDREB2 (Accession number AB016571), ZmGlossy15 (Accession number U41466), and Zmlds1 (Accession number AF048900). The percent identity with ZmABI4 is listed above the schematic for each portion of the sequences.

FIG. 3 shows expression of ZmABI4 in different maize tissues and under different conditions. Panel A shows an RT-PCR analysis of expression of ZmABI4 in leaf (L), in root (R), in tassel (T), and in kernel collected at four, seven, ten and fifteen days after pollination (DAP). Results from the same samples with an RT-PCR control reaction using actin as a constitutive control are also shown.

FIG. 3, Panel B, shows RT-PCR analysis of expression of ZmABI4 and Vp1 in kernel tissue at 5, 10, 15, 20, 25, and 30 days after pollination. Actin is again provided as a constitutive control.

FIG. 4 shows ZmABI4 binding sequences as determined by PCR-assisted binding site selection. The selected sequences are aligned around the consensus CACCG. For the sequences in Group II, reverse complementary stands are presented. For each independent clone, the clone number is indicated on the left. Underlining indicates the two primer sites for the oligo used in the binding site selection. The selected sequences that correspond to Rab17 and HVA22 gene promoter elements (Busk et al. (1997) *Plant Journal* 11(6): 1285–1295; Shen and Ho (1995) *Plant Cell* 7: 295–307) are in bold face and indicated on the right.

FIG. 5 shows binding of ZmABI4 protein to upstream sequences in genes regulated by ZmABI4 and ABA. Panel A shows a sequence alignment of upstream regions of ZmABI4 gene and ABA-regulated genes containing CE1-like sequences, as well as mutated ZmABI4 binding sites used in EMSA analysis. The translation start site is numbered +1, and the sequence of the maize ABI4 gene is shown from −175 to −158. Other sequences shown are the maize Rab28 sequence (−242 to −225; [Busk et al. (1999) *Plant Mol. Biol.* 41(4): 529–536]); barley HVA1 (−81 to −64; [Xiao and Xue (2001) *Plant Cell Rep.* 20: 667–673]); barley HVA22 (−67 to −50; [Shen and Ho (1995) *Plant Cell* 7(3): 295–307]); maize Rab17 DRE2 (−195 to −178; [Busk et al. (1997) *Plant J.* 11(6): 1285–1295]), rice Rab16B (−238 to −221; [Ono et al. (1996) *Plant Physiol.* 112(2): 483–491]), and *C. plantageineum* CdeT27 (−125 to −108; [Michel et al. (1993) *Plant J.* 4(1): 29–40]).

FIG. 5, Panel B shows alignment of the putative TATA box and the ABI4 binding site of ABI4 from *Arabidopsis*, maize and rice.

FIG. 5, Panel C shows Electrophoretic Mobility Shift Assay (EMSA) analysis of ZmABI4 binding to the CE1-like sequences presented in Panel A. Lanes 1–11 represent EMSA reactions with upstream regions of: ZmABI4 (lane 1), mutated ZmABI4-1 (lane 2), mutated ZmABI4-2 (lane 3), mutated ZmABI4-3 (lane 4), mutated ZmABI4-4 (lane 5), rab28 (lane 6), HVA1 (lane 7), HVA22 (lane 8), rab17 (lane 9), rab16B (lane 10), and CdeT27 (lane 11).

FIG. 8 shows that the maize ZmABI4 gene can rescue insensitivity of the abi4 mutant of *Arabidopsis* to growth in the presence of 5 μM ABA or 7% glucose.

Panel A shows wild-type and abi4 mutant plants germinated in the presence of 7% glucose or 5 μM ABA.

Panel B shows rescue of the abi4 mutant phenotype, restoring sensitivity to inhibitory concentrations of glucose by ectopic ZmABI4 expression. Two single-insert, segregating transgenic lines (designated M2 and M6) overexpressing ZmABI4 were surface-sterilized, imbibed five days at 4° C., and transferred to minimal media plates containing 7% glucose. After nine days' growth under constant illumination, seedlings were evaluated for their ability to develop fully expanded cotyledons and green primary leaves. The figure represents the totals from three plates containing more than fifty seeds each; the mean percent of total viable seed is presented, with standard errors. Wild-type seedlings (ecotype Columbia) were unable to form green primary leaves on 7% glucose.

Panel C shows rescue of the abi4 phenotype, restoring sensitivity to ABA by ectopic ZmABI4 expression. Imbibed seeds were spread onto plates containing 5 μM ABA as in 8B and scored following 5d under constant illumination for their ability to develop expanded green cotyledons.

Panel D of FIG. 8 shows that the phenotype of segregating plants corresponds to the presence of ZmABI4. Segregating seedlings grown on 7% glucose medium (from 8B) were grouped into wild-type or mutant phenotypes and placed onto medium without selection. After 10 days of recovery, proteins were extracted, and the presence of the ZmABI4 protein was detected by protein gel blot analysis with a ZmABI4-specific antibody.

Figure 9:
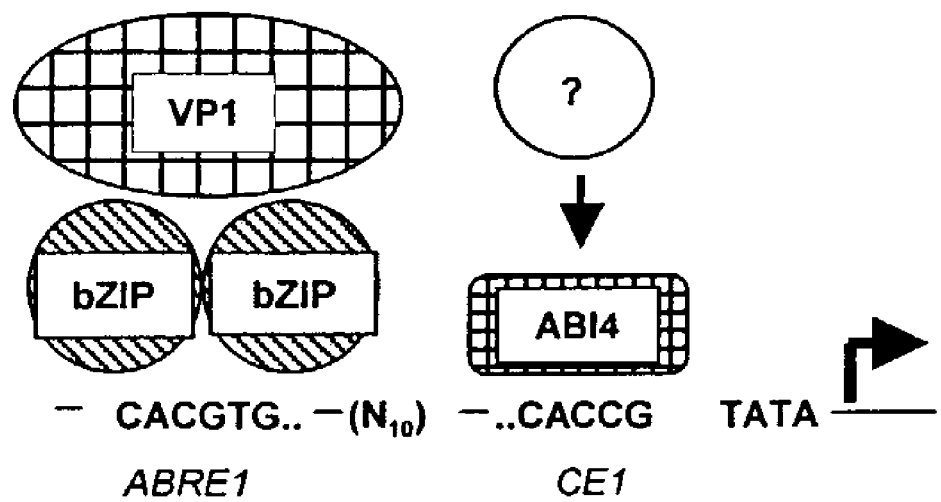

FIG. 9 shows a model for the developmental expression of ABA-responsive genes. In storage-phase embryos, ABI4 binds to the CE1 element, and in conjunction with bZIP, VP1, and other unidentified components, activates storage- and maturation-phase genes, such as rab17.

DETAILED DESCRIPTION OF THE INVENTION

The present invention provides, inter alia, compositions and methods for modulating the total level of proteins of the present invention and/or altering their ratios in a plant. By "modulation" or "modulating" is intended an increase or a decrease in a particular character, quality, substance, or response.

The compositions comprise maize genes and proteins. Particularly, the nucleotide and amino acid sequence for a maize ABI4 gene (SEQ ID NOs: 2, 3, 4, and 5) are provided. SEQ ID NO:2 sets forth the sequence of the coding region of ABI4, while SEQ ID NO:4 includes the coding region as well as a 3' untranslated region of the gene. SEQ ID NO:5 includes 5' and 3' regions in addition to the coding region. SEQ ID NO: 3 provides the amino acid sequence of the encoded ZmABI4 protein. As discussed in more detail below, the sequences of the invention are involved in many basic biochemical pathways that regulate plant stress responses, development, metabolism, and pathogen resistance. Methods are provided for the expression of these sequences in a host plant to modulate plant stress responses, developmental pathways, metabolism, and defense responses. Some of the methods involve stably transforming a plant with a nucleotide sequence capable of modulating the plant metabolism operably linked with a promoter capable of driving expression of a gene in a plant cell.

Also provided are ABI4 promoter sequences set forth in SEQ ID NO:1. Methods are provided for the regulated expression of a nucleotide sequence of interest that is operably linked to the ABI4 promoter sequence disclosed herein. Nucleotide sequences operably linked to the ABI4 promoter are transformed into a plant cell. Exposure of the transformed plant to a stimulus induces transcriptional activation of the nucleotide sequences operably linked to the ABI4 promoter.

Hence the ABI4 promoter sequences may find use in the regulated expression of an operably-linked heterologous gene of interest. For example, the provided sequences may find use in an inducible promoter, such as a stress-inducible promoter. Thus, a fragment of the provided promoter may be used either alone or in combination with other sequences to create synthetic promoter constructs. In such embodiments, the fragments (also called "elements" or "subsequences") confer desired properties on the synthetic promoter construct, such as conferring increased transcription of operably linked sequences in response to drought stress.

A nucleic acid sequence encoding an ABI4 protein from maize is provided. The maize ABI4 sequence shows some homology to ABI4 genes from other plants. The maize ABI4 amino acid sequence shares about 48% identity with the *Arabidopsis* ABI4 coding region.

ABI4 is part of an evolutionarily conserved regulatory system that is involved in cell metabolism and stress response. Thus the sequence of the invention finds use in controlling or modulating cell metabolism as well as the stress response. Transformed plants can be obtained having altered metabolic states as well as altered stress responses; hence, the methods and compositions may find uses in altering the response of plants to different stresses.

Processes affected by the ABI4 gene product include transcription from promoters containing the CACCG motif. Hence, the compositions and methods of the invention find use in the activation or modulation of expression of other genes, including those involved in other aspects of stress response.

Although there is some conservation among genes containing the APETALA2 motif, there are a large number of different proteins that contain the APETALA2 domain, and many of these proteins are large and multifunctional. (See, for example, Jaglo et al., Plant Physiology 127(3):910–917 (2001).) Thus, proteins encoded by members of the APETALA2 gene family may contain different elements or motifs or sequence patterns that modulate or affect the activity, subcellular localization, and/or target of the protein. Such elements, motifs, or sequence patterns may be useful in engineering novel enzymes for reducing or enhancing gene expression in particular tissues.

ABI4 has been shown to be important in pathways involving sugar metabolism, water stress response, and response to extreme temperatures. Expression of the proteins encoded by the sequences of the invention can be used to modulate or regulate the expression of corresponding proteins in these pathways and other directly or indirectly affected pathways. Hence, the compositions and methods of the invention find use in altering plant response to the environment and environmental stimuli. Regulating the expression of ZmABI4 may also alter the metabolic profile of plants and utility may be found in altering the protein, starch or oil composition of plants through ZmABI4 expression. The ZmABI4 gene of the present invention additionally finds use in enhancing the germination of seeds under certain conditions. Alternatively, the ZmABI4 gene of the present invention may find use in repressing the germination of seeds under conditions where germination is undesirable. In other embodiments, fragments of the ZmABI4 gene are used to confer desired properties to synthetic protein constructs for use in regulating plant growth or cellular processes, such as root growth.

Compositions of the invention include the nucleotide sequence of the maize ABI4 gene. The 3' untranslated portion of the maize gene (included in SEQ ID NOS: 4 and 5) may contain regulatory elements useful in modulating expression of operably linked sequences. The polypeptides encoded by the maize ABI4 sequences may be involved in various plant developmental processes, including the plant pathogen defense response. In addition, the ZmABI4 promoter nucleotide sequence is also provided.

The present invention provides for isolated nucleic acid molecules comprising nucleotide sequences encoding the amino acid sequence shown in SEQ ID NO:3. Further provided are polypeptides having an amino acid sequence encoded by a nucleic acid molecule described herein, for example those polypeptides encoded by the sequences set forth in SEQ ID NO: 2, 4 or 5, and fragments and variants thereof.

The present invention further provides for an isolated nucleic acid molecule comprising the sequences shown in SEQ ID NO:2, 4 or 5.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences are encompassed by the present invention. Fragments and variants of proteins encoded by the disclosed nucleotide sequences are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, and/or stress responses by retaining ABI4-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an ABI4 nucleotide sequence that encodes a biologically active portion of an ABI4 protein of the invention will encode at least 12, 25, 30, 35, 40, 45, 50, 55, 60, 65, 70, 75, 80, 85, 90, 95, 100, 110, 125, 135, 150, 165, 175, 185, 200, 215, 225, 235, 250, 260, 275, 285, 300, 315, 325, 334, or 350 contiguous amino acids, or up to the total number of amino acids present in a full-length ABI4 protein of the invention (for example, 248 amino acids for SEQ ID NO:3).

Fragments of an ABI4 nucleotide sequence that are useful as hybridization probes or PCR primers generally need not encode a biologically active portion of an ABI4 protein. Thus, a fragment of an ABI4 coding region nucleotide sequence may encode a biologically active portion of an ABI4 protein. Similarly, a fragment of an ABI4 promoter nucleotide sequence may be biologically active; i.e., the fragment may drive expression of operably linked coding regions. A fragment of an ABI4 nucleotide sequence may also be used as a hybridization probe or PCR primer using methods disclosed below. A biologically active portion of an ABI4 protein can be prepared by isolating a portion of the ABI4 coding region nucleotide sequence of the invention, expressing the encoded portion of the ABI4 protein (e.g., by recombinant expression in vitro), and assessing the activity of the encoded portion of the ABI4 protein. Nucleic acid molecules that are fragments of an ABI4 nucleotide sequence comprise at least 16, 20, 25, 30, 40, 50, 60, 70, 80, 90, 100, 125, 150, 175, 200, 225, 250, 300, 350, 400, 450, 500, 550, 600, 650, 700, 750, 800, 850, 900, 950, 1000, 1050, 1100, 1200, 1300, 1400, 1500, 1600, 1700, 1800, 1900, 2000, 2100, 2200, 2300, 2400, or 2500 nucleotides, or up to the number of nucleotides present in a full-length ABI4 nucleotide sequence disclosed herein (for example, 2521 nucleotides for SEQ ID NO: 1, 747 nucleotides for SEQ ID NO:2, 1145 nucleotides for SEQ ID NO:4).

By "variants" is intended substantially similar sequences. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an ABI4 protein of the invention. Generally, variants of a particular nucleotide sequence of the invention will have at least 40%, 50%, 60%, 70%, generally at least 75%, 80%, 85%, preferably about 90%, 91%, 92%, 93%, 94%, 95%, 96%, 97%, 98%, 99%, or more sequence identity to that particular nucleotide sequence as determined by sequence alignment programs, described elsewhere herein, using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is, they continue to possess the desired biological activity of the native protein, hence they will continue to possess at least one activity possessed by the native ABI4 protein. Such variants may result from, for example, genetic polymorphism or from human manipulation. Biologically active variants of an ABI4 native protein of the invention will have at least 40%, 50%, 60%, 70%, generally at least 75%, 80%, 85%, preferably about 90%, 91%, 92%, 93%, 94%, 95%, 96%, 97%, 98%, 99%, or more sequence identity to the amino acid sequence for the native protein as determined by sequence alignment programs, described elsewhere herein, using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the ABI4 proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ABI4-like activity. It is recognized that variants need not retain all of the activities and/or properties of the native ABI4 protein. Obviously, the mutations that will be made in the DNA encoding the variant must not place the sequence out of reading frame and preferably will not create complementary regions that could produce secondary mRNA structure. See, EP Patent Application Publication No. 0075,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by either an enhanced response to stress or a modulation in a plant developmental or metabolic process when expression of the protein sequence is altered. For example, the activity may be evaluated as a change in sugar metabolism in the plant.

Variant nucleotide sequences and proteins also encompass sequences and proteins derived from a mutagenic and recombinogenic procedure such as DNA shuffling. With such a procedure, one or more different ABI4 coding sequences can be manipulated to create a new ABI4 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the ABI4 gene of the invention and other known ABI4 genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The compositions of the invention also include isolated nucleic acid molecules comprising the promoter nucleotide sequence set forth in SEQ ID NO:1 or SEQ ID NO: 5. By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate.

It is recognized that having identified the nucleotide sequences for the promoter regions disclosed herein, it is within the state of the art to isolate and identify additional regulatory elements in the 5' untranslated region upstream from the particular promoter regions defined herein. Thus for example, the promoter regions disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635,618.

Fragments and variants of the disclosed ABI4 promoter nucleotide sequence are also encompassed by the present invention. By "fragment" is intended a portion of the nucleotide sequence. Fragments of a nucleotide sequence may retain biological activity and hence retain their transcriptional regulatory activity. Thus, for example, less than the entire promoter sequence disclosed herein may be utilized to drive expression of an operably linked nucleotide sequence of interest, such as a nucleotide sequence encoding a heterologous protein. Alternatively, fragments of a nucleotide sequence that are useful as hybridization probes generally do not retain biological activity. Thus, a fragment of an ABI4 promoter nucleotide sequence may encode a biologically active portion of the ABI4 promoter, or it may be a fragment that can be used as a hybridization probe or PCR primer using methods disclosed below. Nucleic acid molecules that are fragments of an ABI4 promoter comprise a nucleotide sequence of at least about 16 to 20 nucleotides to about 30, 40, 50, 60, 70, 80, 90, 100, 150, 200, 250, 300, 350, 400, 450, 500, 550, 600, 650, 700, 750, 800, 850, 900, 950, 1000, 1050, 1100, 1200, 1300, 1400, 1500, 1600, 1700, 1800, 1900, 2000, 2100, 2200, 2300, 2400, or 2500 nucleotides, or up to the number of nucleotides present in a full-length ABI4 nucleotide sequence disclosed herein (for example, 2521 nucleotides for SEQ ID NO: 1).

A biologically active portion of an ABI4 promoter can be prepared by isolating a portion of one of the ABI4 promoter nucleotide sequences of the invention, and assessing the activity of the portion of the ABI4 promoter. Assays to determine the activity of a promoter sequence are well known in the art. For example, an ABI4 promoter fragment or variant may be operably linked to the nucleotide sequence encoding any reporter protein, such as the β-glucuronidase protein (GUS reporter) or the luciferase protein. The DNA construct is inserted into the genome of a plant or plant cell and the mRNA or protein level of the reporter sequence is determined. See, for example, Eulgem et al. (1999) *EMBO Journal* 18: 4689–4699.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have ABI4 promoter activity or encode an ABI4 protein and which hybridize under stringent conditions to the ABI4 sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to corresponding stress-response sequences and messenger RNAs. To achieve specific hybridization under a variety of conditions, such probes include sequences that are unique among stress-response sequences and are preferably at least about 10 or 15 or 17 nucleotides in length, and most preferably at least about 20 or 22 or 25 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration may be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, nucleotide sequences that have promoter activity or encode an ABI4 protein and which hybridize to the ABI4 sequences disclosed herein will be at least about 40% homologous, about 50% or 60% homologous, about 70% homologous, and even about 80%, 85%, 90%, 91%, 92%, 93%, 94%, 95%, 98%, 99% or more homologous with the disclosed sequences. That is, the sequence identity of the sequences may be from about 40% to 50% identical, about 60% to 70% or 75%, and even about 80%, 85%, 87%, 90%, 91%, 92%, 93%, 94%, 95%, 96%, 97%, 98%, or 99% identical, or higher, so that the sequences may differ by only one amino acid residue or one nucleic acid.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment-may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions-are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95% sequence identity.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Compositions and methods for controlling pathogenic agents are provided. The anti-pathogenic compositions comprise ABI4 promoters as well as genes and proteins. Particularly, the maize ABI4 promoter, genes and proteins are provided. Accordingly, the compositions and methods are useful in protecting plants against stress, including stress caused by the attack or infection of fungal pathogens, viruses, nematodes, insects and the like. In this manner, the invention provides disease resistance and pathogen resistance.

By "disease resistance" or "pathogen resistance" is intended that the plants avoid the disease symptoms which are the outcome of plant-pathogen interactions. That is, pathogens are prevented from causing plant diseases and the associated disease symptoms, or alternatively, the disease symptoms caused by the pathogen is minimized or lessened.

An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Altemaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani*; Canola: *Albugo candida, Altemaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Altemaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondite* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Scierotinia sclerotiorum,* Aster Yellows, *Septoria helianthi, Phomopsis helianthi, Altemaria helianthi, Altemaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Maize: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including *Heterodera* and *Globodera* spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; Anuraphis maidiradicis, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exclamationis, sunflower beetle; *Bothyrus gibbosus*, carrot beetle; *Neolasioptera murtfeldiana*, sunflower seed midge; Cotton: *Heliothis virescens,*cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucoptenis leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

By "anti-pathogenic compositions" is intended that the compositions of the invention are capable of suppressing, controlling, and/or killing the invading pathogenic organism or insect pest.

Methods for increasing pathogen resistance in a plant are provided. The methods involve stably transforming a plant with a DNA construct comprising an anti-pathogenic nucleotide sequence of the invention operably linked to promoter that drives expression in a plant. Such methods may find use in agriculture particularly in limiting the impact of plant pathogens or insect pests on crop plants. The anti-pathogenic nucleotide sequences comprise the maize ABI4 nucleic acid molecules. While the choice of promoter will depend on the desired timing and location of expression of the anti-pathogenic or other nucleotide sequences, desirable promoters include constitutive and pathogen-inducible promoters. In this manner, the maize ABI4 promoter may provide suitable regulation of expression of operably linked coding regions to control pathogen and insect pests.

Additionally, the compositions can be used in formulation use for their disease resistance activities. The proteins of the invention can be formulated with an acceptable carrier into a pesticidal composition(s) that is for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Additionally, transformed plants, plant cells, plant tissues and seeds thereof are provided.

It is understood in the art that plant DNA viruses and fungal pathogens remodel the control of the host replication and gene expression machinery to accomplish their own replication and effective infection. The present invention may be useful in preventing such corruption of the cell.

As discussed above, ABI4 is involved in many basic biochemical pathways and cellular functions that influence the plant stress response. Hence, the sequences of the invention may find use in disrupting cellular function of plant pathogens or insect pests as well as altering the defense mechanisms of a host plant to enhance resistance to disease or insect pests.

While the invention is not bound by any particular mechanism of action, the gene products, probably proteins or polypeptides, function to inhibit or prevent plant diseases in a plant. Such gene products may be anti-pathogenic. That is such gene products may be capable of suppressing, controlling, and/or killing the invading pathogenic organism. Further, the promoters of the invention may provide control of gene expression which may be helpful in avoiding or ameliorating disease symptoms. It is recognized that the present invention is not dependent upon a particular mechanism of defense. Rather, the compositions and methods of the invention work to increase resistance of the plant to pathogens independent of how that resistance is increased or achieved.

The methods of the invention can be used with other methods available in the art for enhancing disease resistance in plants. Similarly, the plant defense mechanisms described herein may be used alone or in combination with other proteins or agents to protect against plant diseases and pathogens. Other plant defense proteins include those described in copending applications entitled "Methods for Enhancing Disease Resistance in Plants", U.S. application Ser. No. 09/256,898, filed Feb. 24, 1999, and copending application entitled "Genes for Activation of Plant Pathogen Defense Systems", U.S. application Ser. No. 09/256,158, filed Feb. 24, 1999, which are herein incorporated by reference.

The present invention may be used in conjunction with one or more other methods to increase disease resistance. Although any one of a variety of second nucleotide sequences may be utilized, some embodiments of the invention encompass those second nucleotide sequences that, when expressed in a plant, help to increase the resistance of a plant to pathogens. It is recognized that such second nucleotide sequences may be used in either the sense or antisense orientation depending on the desired outcome.

Additionally, the ABI4 promoter nucleotide sequences disclosed herein are also useful for genetic engineering of plants to express a phenotype of interest. The promoter sequences may be used to drive expression of any heterologous nucleotide sequence. Alternatively, the ABI4 promoter sequence may be used to drive expression of its native, i.e., naturally occurring, ABI4 gene sequence disclosed herein; in such an embodiment, the phenotype of the plant is altered. In some embodiments, the ABI4 promoter sequences are operably linked to an anti-pathogenic nucleotide sequence and drive expression of said sequence in a plant cell. The ABI4 promoter sequences may therefore be used in creating or enhancing pathogen or disease resistance in a transformed plant.

The ABI4 sequences of the invention are provided in expression cassettes or DNA constructs for expression in the plant of interest. The cassette will include 5' and 3' regulatory sequences operably linked to an ABI4 sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the ABI4 sequence to be under the transcriptional regulation of the regulatory regions. The expression cassette may additionally contain selectable marker genes.

The expression cassette will include in the 5'-3' direction of transcription, a transcriptional and translational initiation region, an ABI4 DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of the ABI4 protein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci.* 86:2549–2553; Deuschle et al. (1990) *Science* 248:480483; Gossen (1993) Ph.D. Thesis, University of Heidelberg; Reines et al. (1993) *Proc. Natl. Acad. Sci.* 90:1917–1921; Labow et al. (1990) *Mol. Cell. Biol* 10:3343–3356; Zambretti et al. (1992) *Proc. Natl. Acad. Sci.* 89:3952–3956; Baim et al. (1991) *Proc. Natl. Acad. Sci.* 88:5072–5076; Wyborski et al. (1991) *Nucleic Acids Res.* 19:4647–4653; Hillenand-Wissman (1989) *Topics Mol. Struc. Biol.* 10:143–162; Degenkolb et a. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci.* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334: 721–724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also the copending applications entitled "Inducible Maize Promoters", U.S. patent application Ser. No. 09/257,583, filed Feb. 25, 1999, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci.* 83:2427–2430; Somsisch et al. (1988) *Mol. Gen. Genet.* 2:93–98; and Yang (1996) *Proc. Natl. Acad. Sci.* 93:14972–14977. See also, Chen et al. (1996) *Plant J.* 10:955–966; Zhang et al. (1994) *Proc. Natl. Acad. Sci.* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc.*

Natl. Acad. Sci. USA 88:10421–10425 and McNellis et al. (1998) Plant J. 14(2):247–257) and tetracycline-inducible and tetracycline-repressible promoters (see, for example, Gatz et al. (1991) Mol. Gen. Genet 227:229–237, and U.S. Pat. Nos. 5,814,618 and 5,789,156), herein incorporated by reference.

Tissue-preferred promoters can be utilized to target enhanced ABI4 expression within a particular plant tissue. Tissue-preferred promoters include Yamamoto et al. (1997) Plant J. 12(2):255–265; Kawamata et al. (1997) Plant Cell Physiol. 38(7):792–803; Hansen et al. (1997) Mol. Gen Genet. 254(3):337–343; Russell et al. (1997) Transgenic Res. 6(2):157–168; Rinehart et al. (1996) Plant Physiol. 112(3):1331–1341; Van Camp et al. (1996) Plant Physiol. 112(2):525–535; Canevascini et al. (1996) Plant Physiol. 112(2):513–524; Yamamoto et al. (1994) Plant Cell Physiol. 35(5):773–778; Lam (1994) Results Probl. Cell Differ. 20:181–196; Orozco et al. (1993) Plant Mol Biol. 23(6): 1129–1138; Matsuoka et al. (1993) Proc Natl. Acad. Sci. USA 90(20):9586–9590; and Guevara-Garcia et al. (1993) Plant J. 4(3):495–505. Such promoters can be modified, if necessary, for weak expression.

Leaf-specific promoters are known in the art. See, for example, Yamamoto et al. (1997) Plant J. 12(2):255–265; Kwon et al. (1994) Plant Physiol. 105:357–67; Yamamoto et al. (1994) Plant Cell Physiol. 35(5):773–778; Gotor et al. (1993) Plant J. 3:509–18; Orozco et al. (1993) Plant Mol. Biol. 23(6):1129–1138; and Matsuoka et al. (1993) Proc. Natl. Acad. Sci. USA 90(20):9586–9590.

Root-preferred promoters are known and can be selected from the many available from the literature or isolated de novo from various compatible species. See, for example, Hire et al. (1992) Plant Mol. Biol. 20(2):207–218 (soybean root-specific glutamine synthetase gene); Keller and Baumgartner (1991) Plant Cell 3(10):1051–1061 (root-specific control element in the GRP 1.8 gene of French bean); Sanger et al. (1990) Plant Mol. Biol. 14(3):433–443 (root-specific promoter of the mannopine synthase (MAS) gene of Agrobacterium tumefaciens); and Miao et al. (1991) Plant Cell 3(1):11–22 (full-length cDNA clone encoding cytosolic glutamine synthetase (GS), which is expressed in roots and root nodules of soybean). See also Bogusz et al. (1990) Plant Cell 2(7):633–641, where two root-specific promoters isolated from hemoglobin genes from the nitrogen-fixing nonlegume Parasponia andersonii and the related non-nitrogen-fixing nonlegume Trema tomentosa are described. The promoters of these genes were linked to a β-glucuronidase reporter gene and introduced into both the nonlegume Nicotiana tabacum and the legume Lotus corniculatus, and in both instances root-specific promoter activity was preserved. Leach and Aoyagi (1991) describe their analysis of the promoters of the highly expressed roIC and roID root-inducing genes of Agrobacterium rhizogenes (see Plant Science (Limerick) 79(1):69–76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8(2): 343–350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29(4): 759–772); and roIB promoter (Capana et al. (1994) Plant Mol. Biol. 25(4):681–691. See also U.S. Pat. Nos. 5,837, 876; 5,750,386; 5,633,363; 5,459,252; 5,401,836; 5,110, 732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40 (U.S. Pat. No. 6,403,862); nuc1c (U.S. Pat. No. 6,407,315); and celA (cellulose synthase) (see WO 00/11177, herein incorporated by reference). Gama-zein is an endosperm-specific promoter. Glob-1 is an embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Where low level expression is desired, weak promoters will be used. Generally, by "weak promoter" is intended a promoter that drives expression of a coding sequence at a low level. By low level is intended at levels of about $1/1000$ transcripts to about $1/100,000$ transcripts to about $1/500,000$ transcripts. Alternatively, it is recognized that weak promoters also encompass promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the ABI4 protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923–926); and Lec1 transformation (WO 00/28058). Also see Weissinger et al. (1988) *Ann. Rev. Genet* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) In *Vitro Cell Dev. Biol.* 27P: 175–182 (soybean); Singh et al. (1998) *Theor. Appl. Genet.* 96:319–324 (soybean); Dafta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and resulting plants having desired expression of the subject phenotypic characteristic may be identified. Two or more generations may be grown to ensure that the desired expression of the subject phenotypic characteristic is stably maintained and inherited and then seeds harvested to ensure that desired expression of the subject phenotypic characteristic has been achieved.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* 1spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

It is recognized that with these nucleotide sequences, antisense constructions, complementary to at least a portion of the messenger RNA (mRNA) for the ABI4 sequences can be constructed. Antisense nucleotides are constructed to hybridize with the corresponding mRNA. Modifications of the antisense sequences may be made, as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The nucleotide sequences for the ABI4 promoters disclosed in the present invention, as well as variants and fragments thereof, are useful in the genetic manipulation of any plant when assembled with a DNA construct such that the promoter sequence is operably linked to a nucleotide sequence encoding a heterologous protein of interest. In this manner, the nucleotide sequences of the ABI4 promoter of the invention are provided in expression cassettes along with heterologous nucleotide sequences for expression in the plant of interest.

The promoter for the ABI4 gene may regulate expression of operably linked nucleotide sequences in an inducible manner. That is, expression of the operably linked nucleotide sequences in a plant cell is induced in response to a stimulus. By "stimulus" is intended a chemical, which may be applied externally or may accumulate in response to another external stimulus; other stresses such as environmental stresses, including but not limited to drought, temperature, and salinity; or other factor such as a pathogen, which may, for example, induce expression as a result of invading a plant cell.

Synthetic promoters are known in the art. Such promoters comprise upstream promoter elements (also referred to as "fragments" or "subsequences") of one nucleotide sequence operably linked to at least one promoter element of another nucleotide sequence. In an embodiment of the invention, heterologous gene expression is controlled by a synthetic hybrid promoter comprising the ABI4 promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton and Somssich. (1998) *Curr. Opin. Plant Biol.* 1:311–315. Alternatively, a synthetic ABI4 promoter sequence may comprise duplications of upstream elements found within the ABI4 promoter sequence.

It is recognized that the promoter sequence of the invention may be used with its native ABI4 coding sequences. A DNA construct comprising the ABI4 promoter operably linked with its native ABI4 gene may be used to transform any plant of interest to bring about a desired phenotypic change, such as enhanced disease resistance. Where the promoter and its native gene are naturally occurring within the plant, i.e., in maize, transformation of the plant with these operably linked sequences also results in either a change in phenotype such as enhanced stress response or the insertion of operably linked sequences within a different region of the chromosome, thereby altering the plant's genome.

In another embodiment of the invention, expression cassettes will comprise a transcriptional initiation region comprising the ABI4 promoter nucleotide sequences disclosed herein, or variants or fragments thereof, operably linked to the heterologous nucleotide sequence whose expression is to be controlled by the inducible promoter of the invention. In some embodiments, expression cassettes will further comprise sequence elements that modulate expression or activity of operably linked sequences. For example, the 3' untranslated region of the ABI4 gene (included in SEQ ID NO:4) may contain elements that can modulate expression of operably linked coding regions.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's response to drought stress, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be molecularly altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. application Ser. No. 08/838,763, filed Apr. 10, 1997; Ser. No. 08/824,379, filed Mar. 26, 1997; Ser. No. 08/824,382, filed Mar. 26, 1997; and U.S. Pat. No. 5,703,049; herein incorporated by reference. Another example is lysine and/or sulfur rich seed protein encoded by the soybean 2S albumin described in U.S. application Ser. No. 08/618,911, filed Mar. 20, 1996, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and PCT/US97/20441, filed Oct. 31, 1997, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs,* ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in copending U.S. application Ser. No. 08/838,763, filed Apr. 10, 1997, and U.S. Pat. Nos. 5,703,049, 5,885,801, and 5,885,802.

Commercial traits can also be encoded on a gene or genes that could increase, for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) *J. Bacteriol.* 170:5837–5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

In certain embodiments the nucleic acid sequences of the present invention can be stacked with any combination of polynucleotide sequences of interest in order to create plants with a desired phenotype. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99–106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266: 789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837–5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combine with any combination of other suppression cassettes or overexpression cassettes to generate the desired combination of traits in the plant.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol Rep.* 9:104–126; Clark et al. (1989) *J. Biol. Chem.* 264:17544–17550; Della-Cioppa et aL. (1987) *Plant Physiol.* 84:965–968; Romer et al. (1993) *Biochem. Biophys. Res. Commun.* 196:1414–1421; and Shah et al. (1986) *Science* 233:478–481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769–780; Schnell et al. (1991) *J. Biol. Chem.* 266(5):3335–3342); 5-(enolpyruvyl)shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11):6081–6087); plastocyanin (Lawrence et al. (1997) *J. Biol. Chem.* 272 (33):20357–20363); chorismate synthase (Schmidt et al. (1993) *J. Biol. Chem.* 268(36):27447–27457); and the light harvesting chlorophyll a/b binding protein (LHBP) (Lamppa et al. (1988) *J. Biol. Chem.* 263:14996–14999). See also Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

Methods for transformation of chloroplasts are known in the art. See, for example, Svab et al. (1990) *Proc. Natl. Acad. Sci. USA* 87:8526–8530; Svab and Maliga (1993) *Proc. Natl. Acad. Sci.* 90:913–917; Svab and Maliga (1993) *EMBO J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci.* 91:7301–7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci.* 96:8774–8778; herein incorporated by reference.

The following examples are offered by way of illustration and not by way of limitation.

EXPERIMENTAL

Example 1

Isolation and Sequence Analysis of the ZmAbi4 Gene

Three ESTs with high homology to the AP2 domain of the *Arabidopsis* ABI4 gene were identified from the DuPont/Pioneer database. All three ESTs were from 20 DAP (days after pollination) maize embryo libraries and represent transcripts of the same gene. Following sequencing of the full insert from the longest clone, an open reading frame (ORF) of 747 bps was detected that, when translated, included the AP2 domain in frame. This sequence was subsequently used to isolate an upstream fragment of 2521 bp 5' of the ATG start codon by genome walking using the Universal GenomeWalker™ Kit (Clontech, Palo Alto, Calif.). The sequence upstream of the ORF contained several potential TATA boxes, including one located 71 bp upstream of the longest cDNA (FIG. 1). Genomic sequence analysis by PCR also indicated the maize ABI4 homolog has no intron. Based on sequence homology we designated the maize homolog as ZmABI4.

The deduced amino acid sequence revealed a significant degree of identity between the ZmABI4 and AtABI4 protein in the AP2 domain (50/55 identical). The ZmABI4 protein is smaller, however, and outside of the AP2 domain the sequence was divergent (FIG. 2A). The overall structural features of AtABI4 were largely present in ZmABI4, however. For example, a Ser/Thr rich sequence was present (9/24 residues, compared to 19/28 for *Arabidopsis*) as was a small Q-rich domain (3/14 residues, compared to 13/21). The C-terminal half of the ZmABI4 protein was Pro-rich, but a defined proline domain was missing from the maize sequence. Lastly, the C-terminal 40 residues were high in acidic residues, similar to the *Arabidopsis* sequence. The identity between ZmABI4 and AtABI4 in the AP2 domain was significantly higher than between ZmABI4 and other AP2 domain proteins in maize or *Arabidopsis* (FIG. 2B), indicating that, within the public and DuPont/Pioneer databases, the protein sequence presented here is the closest structural homolog of the *Arabidopsis* ABI4 protein. The identity of the maize ABI4 AP2 domain with that found in *Oryza sativa* ABI4 (See FIG. 2B) provides further confirmation of the sequence as ZmABI4.

Example 2

Determination of Map Position of ZmABI4

The ZmABI4 clone was mapped on the maize genome and found to be located in Bin 6.05, which has been shown to be the location of significant quantitative trait loci (QTL) in previous studies for ABA response, anthesis-silking interval, and drought stress response. See, Quarrie et al. (1999) *J. Exp. Bot.* 50:1299–1306; Frova et al., (1998) *J. Exp. Zoo.* 282:164–170; Ribaut et al., (1996) *Theor. Appl. Genet* 92:905–914; Sanguineti et al., (1999) *J. Exp. Bot.* 50:1289–1297; Pekic and Quarrie (1988) *Annals Bot.* 61:669–678; Tuberosa et al. (1998) *Theor. Appl. Genet.* 97:744–755. In addition, the rab17 gene, which is stress- and ABA-responsive, also maps to the same chromosomal location. The *Arabidopsis* ABI4 gene is located on the lower arm of chromosome 2 (Finkelstein and Goodman (1998) *Plant Cell* 10:1043–1054) and is clustered with a number of other ABA-related genes (Wang et al. (1999) *Genome Res.* 9(4): 325–333). Taken together, the maize QTL data and the ABI4 regulatory locus in *Arabidopsis* suggest that this region of the genome performs an important function for seed development and stress responses in these divergent plant species.

Example 3

Expression of the ZmABI4 Gene

The ZmABI4 sequence is only present in libraries from 20DAP kernels, suggesting that this putative regulatory protein may be important for the regulation of the storage phase of maize kernel development. In order to characterize the expression pattern of this gene in more detail, we used RT-PCR analysis to quantify ZmABI4 transcript in different tissues. Message for this gene was difficult to reliably detect by Northern blotting in maize (data not shown); RT-PCR is a more sensitive method to detect low abundance transcripts. RT-PCR analysis of vegetative tissues demonstrated that the ZmABI4 message was undetectable in any of the tissues tested, in contrast to *Arabidopsis*, where AtABI4 is present at low levels in vegetative tissue. In addition, treatment of vegetative tissues with ABA or high sugars did not induce transcript accumulation to detectable levels (data not shown) as has been shown in *Arabidopsis* (Soderman et al. (2000) *Plant Physiol.* 124(4): 1752–1765). These results indicate that, within the level of detection of RT-PCR, ZmABI4 message was not present in vegetative tissues under the conditions tested. During kernel development, ZmABI4 mRNA is detectable as early as 10 DAP, but accumulates between 10 and 15 DAP (FIG. 3A). RT-PCR analysis of message levels throughout seed development and maturation indicated that ZmABI4 mRNA levels began to accumulate at the transition to the storage phase of kernel development (starting after about 12 DAP) and continued through maturation.

Additional RT-PCR analysis was performed to determine if ZmABI4 message was induced in response to ABA or high sugar levels during seed development. Ten-DAP kernels were excised from inbred maize plants and incubated for 24 h in MS media containing high and low levels of glucose or sucrose (7% and 2% respectively) as well as MS media plus 2% glucose or sucrose with additional ABA (10 μM). No increase in ZmABI4 message level was detected.

Example 4

Determination of the ZmABI4 Binding Sites

Expression analysis suggested that ZmABI4 is involved in responding to developmental, hormonal and/or carbohydrate signals to initiate or regulate the storage phase of seed development in maize. Studies of *Arabidopsis* ABI4 have shown that AtABI4 is involved in both ABA and sugar signaling processes, and a number of genes responsive to sugar and ABA are affected in the ABI4 mutant. Because AtABI4 is a plant AP2-type transcription factor, ABI4 could conceivably regulate these genes by direct interaction with their cognate promoters. In order to determine the sequences that ABI4 protein may bind to and to gain a greater understanding of the function of the ABI4 protein, a PCR-assisted binding site selection method was used to determine the binding site for this putative DNA binding protein. Recombinant ZmABI4 protein was incubated with a library of random double-stranded oligonucleotides in a binding reaction. Following gel electrophoresis, the shifted DNA band was excised from the gel, purified and subjected to PCR amplification. This procedure was repeated five additional times to enrich the sequences bound by the ZmABI4 protein. The enriched sequences from the last round of selection were cloned, and 52 independent clones were sequenced. The selected sequences are shown in FIG. 4. Of 52 sequences, most (42) had the 5 bp consensus sequence CACCG, suggesting that the ZmABI4 protein has affinity for this pentamer sequence (FIG. 4). Screening the literature and using the PLACE database (http://www.dna.affrc.go.jp/htdocs/PLACE/), we found that the CE1 site, a cis-element previously shown to be functionally important to ABA-regulated gene expression (Shen and Ho (1995) *Plant Cell* 7(3): 295–307), resembles the ZmABI4 binding site. The CE1 element is present in a number of ABA-regulated genes (FIG. 5). Interestingly, a putative binding site is also present in the ZmABI4 upstream region (FIG. 5), suggesting the possibility of an auto-regulatory function for the ABI4 protein.

To confirm the binding of ZmABI4 to the selected site, dsDNA probes were created corresponding to the CE-like sequences found in ABA-related genes from a range of species. FIG. 5C shows that recombinant ZmABI4 protein bound to a range of promoter elements including those from the maize ABI4, maize rab28, maize rab17, barley HVA22, barley HVA1, rice rab16b, and *C. plantagineum* CdeT27 genes. Among these promoter elements, HVA22 CE1 and Rab17 DRE2 elements have been shown to be important for ABA induction (Shen and Ho (1995) *Plant Cell* 7(3): 295–307; Busk et al. (1997) *Plant J.* 11(6): 1285–1295).

Figure 6:
FIG. 6 shows EMSA analysis of ZmABI4 binding to ADH1 promoter and alignment of promoter elements of sugar-regulated genes in *Arabidopsis*. Panel A shows binding of maize ABI4 protein to ABI4 binding site in the maize ADH1 gene (AF123535). ADH1 sequence (−246 CGC-CGCCACCGCTTGGCG −229, ABI4 binding site is in bold) was used for gel shift reactions (lanes 3,6). ABI4 (lanes 1,4) and Mut-2 sequences (lanes 2,5) were used as controls (see FIG. 5A). Lanes 1–3 and 4–6 are reactions without or with ZmABI4 protein, respectively. Panel B shows the alignment of the CE/DRE motifs from various *Arabidopsis thaliana* genes. These motifs, found here in *Arabidopsis* sugar-related genes, are potential ABI4 binding sites. Shown are motifs from: ADH1 (GenBank #X77943), Em1 (GenBank #Z11158), Em6 (GenBank #Z11157), ApL3 (GenBank #Y18432), and PC (GenBank #S67901). Numbering is relative to the transcription start site, except for ApL3, which is numbered relative to the start of translation.

Recent studies have also shown that AtABI4 is also involved in sugar sensing in *Arabidopsis*, with the suggestion that ABI4 functions to regulate the storage mode in response to a sugar signal, mediated through ABA (Rook et al. (2001) *Plant J.* 26(4): 421–433). The maize AdhI gene is known to be regulated by sugar (Koch et al. (2000) *J. Exp. Bot* 51 (Spec. No): 417–427; Niu and Bate, unpublished data). Analysis of the maize Adh1 promoter revealed the presence of an ABI4 binding site. FIG. 6A shows that recombinant ABI4 binds to the Adh1 promoter with high affinity. Further analysis of the upstream sequences and promoter regions of a number of *Arabidopsis* sugar-responsive genes revealed the presence of ABI4 binding sites (FIG. 6B). These genes have also been shown to have modified expression in the *Arabidopsis* abi4 mutant.

Figure 7:
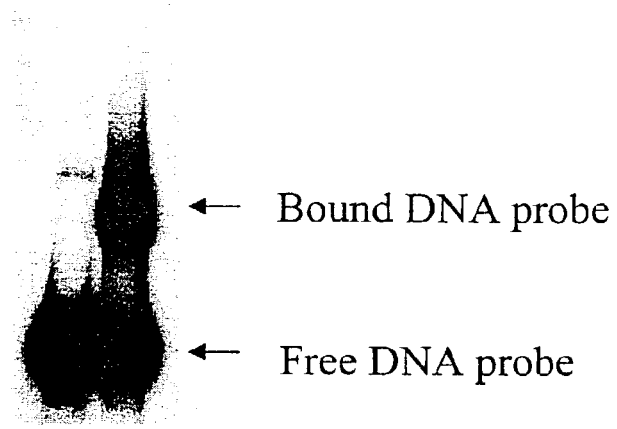
FIG. 7, Panel A shows binding of maize ABI4 protein to the *Arabidopsis* ABI gene upstream region. The labeled 675 bp DNA fragment used in this EMSA assay was from −778 to −104 of the maize ABI4 gene (numbering relative to translation start site). Panel B shows the alignment of the maize and *Arabidopsis* sequences around the TATA box, showing that the ABI4 binding site is in a similar location in both genes

As evidenced from the binding site selection experiment and EMSA assays of ZmABI4 binding to dsDNA CE1-like elements, the sequence CACCGC is a strong binding site for ZmABI4. FIG. 7A shows that ZmABI4 binds to the CACCG site present in its own promoter. A consensus sequence for the ABI4 binding site is present in the *Arabidopsis* gene immediately downstream from a putative TATA box as observed in the maize upstream region (FIG. 7B). The existence of putative binding sites in the same relative location in these diverse species suggests a mechanism of auto-regulatory control. The significance of the location of this site may lay in the supposition that protein binding immediately downstream of the TATA box is effective at suppressing transcriptional elongation (Heins et al. (1992) *Mol. Gen. Genet.* 232:328–331), suggesting that ABI4 binding to its own promoter is a means to suppress its transcription.

Example 5

Rescue of the *Arabidopsis* abi4 Mutant with ZmAbi4

Significant homology between AtABI4 and ZmABI4, particularly in the AP2 domain, suggests that these proteins may play an orthologous role in the regulation of sugar- and ABA-inducible genes. In order to demonstrate functional equivalence, the ZmABI4 gene, under the control of a constitutive promoter (the maize Ubiquitin promoter, with glufosinate resistance as the selectable marker) was transferred into the abi4-1 mutant of *Arabidopsis* (obtained from the ABRC stock center). A number of primary transformants were selected by glufosinate resistance, and seeds from these plants were used to establish copy number by glufosinate resistance. Two independent single-insert lines of abi4/Ubi:ZmABI4 were selected for further characterization. In order to establish the ability of the ZmABI4 gene to rescue *Arabidopsis* abi4 mutation, an abi4 mutant line segregating for the presence of the Ubi::ZmAbi4 transgene was grown in the presence of repressive concentrations of ABA (5 µM) or glucose (7%).

When germinated in the presence of 5 µM ABA, wild-type plants produced a radicle, but did not develop further (FIG. 8A, right panel). Similarly, wild-type plants germinated in the presence of 7% glucose germinated and expanded their cotyledons but did not produce green true leaves (FIG. 8A, left panel). Early development of seedlings under these repressive conditions therefore provided an effective screen to assess the ability of the ZmABI4 gene to rescue the phenotype of the *Arabidopsis* abi4 mutation. Surface-sterilized mutant seeds segregating for the presence of the transgene were placed onto minimal media plates containing 7% glucose (FIG. 8B) or 5 µM ABA (FIG. 8C). Single-insert lines segregating for the transgene would have a 3:1 ratio of wild-type to mutant phenotype if the ZmABI4 rescues the *Arabidopsis* abi4 mutation. If the transgene does not rescue the *Arabidopsis* mutant, the seedlings would all have the mutant phenotype.

FIG. 8C indicates that in two independent lines of abi4 mutant *Arabidopsis*, ectopic expression of the ZmABI4 gene at least partially compensated for the genetic lesion in *Arabidopsis* abi4. Approximately 75% of the seedlings had the wild-type phenotype when grown on 5 µM ABA.

Screening the same segregating population for the ability to germinate and form true green leaves in the presence of inhibitory concentrations of glucose gave similar results (FIG. 8B). Mutant seed lines containing a segregating transgene were treated as above, except that 7% glucose was the inhibitory reagent. Plants were imbibed for five days to ensure that germination was initiated before plating. Both transgenic lines rescued the mutant phenotype in a ratio close to the expected 3:1 (FIG. 8B).

Seedlings with the wild-type and mutant phenotype were removed from the 7% glucose plates and placed onto minimal media plates containing 2% glucose. Following one week of recovery, the plants were assayed for the presence of the transgene by Western blot analysis with a ZmABI4-specific antibody. None of the plants (eight out of eight surveyed) with a mutant phenotype contained the transgene, whereas seven out of eight seedlings with the wild-type phenotype when grown on 7% glucose possessed a functional transgene (FIG. 8D).

In order to further characterize the rescue of the *Arabidopsis* abi4 mutation by ZmABI4, the effect on target gene expression in mutant plants homozygous for the transgene was determined. ABA induced the expression of genes for seed storage proteins in the vegetative tissues of plants ectopically expressing AtABI4 under the control of the ubiquitin promoter (Christensen et al. (1992) *Plant Mol. Biol.* 18:675–689). Homozygous ZmABI4 transgenic seedlings transferred to media containing 5 μM ABA expressed cruciferin and Em6 in vegetative tissues, whereas wild-type and abi4 mutants did not. Similarly, plants with constitutive expression of ZmABI4 responded to growth on 7% sucrose by inducing the expression of ApL3 (encoding the large subunit of ADP-glucose pyrophosphorylase; Villand et al. (1993) *Plant Mol. Biol.* 23: 1279–1284) to similar levels as seen with wild-type plants. ABI4 mutant plants did not induce the expression of ApL3. These results demonstrate that ZmABI4 performs two functions associated with *Arabidopsis* Abi4: the induction of seed storage protein genes as well as induction of the sugar responsive gene ApL3.

Example 6

Transformation and Regeneration of Transgenic Plants

Immature maize embryos from greenhouse donor plants are bombarded with a plasmid comprising a ZmABI4 polynucleotide operably linked to a promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a ZmABI4 polynucleotide operably linked to a promoter is made. This plasmid DNA, plus plasmid DNA containing a PAT selectable marker, is precipitated onto 1.1 μm (average diameter) tungsten pellets using a $CaCl_2$ precipitation procedure as follows:

100 μl prepared tungsten particles in water

10 μl (1 μg) DNA in Tris EDTA buffer (1 μg total DNA)

100 μl 2.5 M $CaCl_2$

10 μl 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for altered response to increased salinity or other environmental stress.

Bombardment and Culture Media

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 7

Agrobacterium-Mediated Transformation

For *Agrobacterium*-mediated transformation of maize with a ZmABI4 polynucleotide operably linked to a promoter, preferably the method of Zhao is employed (U.S. Pat. No. 5,981,840, and PCT patent publication WO98/32326, the contents of both of which are hereby incorporated by reference). Briefly, immature embryos are isolated from maize and the embryos contacted with a suspension of *Agrobacterium*, where the bacteria are capable of transferring the ABI4 construct to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 8

Soybean Embryo Transformation

Soybean embryos are bombarded with a plasmid containing the ABI4 gene operably linked to a synthetic promoter comprising ABI4 promoter sequences as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker at 150 rpm and 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic PDS1000®/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the ZmABI4 gene operably linked to a synthetic promoter comprising ZmABI4 promoter sequences can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/pl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm Petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Sunflower Meristem Tissue Transformation

Sunflower meristem tissues are transformed with an expression cassette containing the ABI4 gene operably linked to a synthetic promoter comprising ABI4 promoter sequences as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox™ bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant* 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to *Agrobacterium* treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm Nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ABI4 gene operably linked to a synthetic promoter comprising ABI4 promoter sequences is introduced into *Agrobacterium* strain EHA105 via freeze-thawing as described by Holsters et al. (1978) *Mol. Gen. Genet.* 163:181–187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for ABI4 activity, for example, assaying altered responsiveness to conditions of increased salinity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with Parafilm™ film to secure the shoot. Grafted plants can be transferred to soil following one week of in vitro culture. Grafts in soil are maintained under high humidity conditions followed by a slow acclimatization to the greenhouse environment. Transformed sectors of To plants (parental generation) maturing in the greenhouse are identified by NPTII ELISA and/or by ABI4 activity analysis of leaf extracts while transgenic seeds harvested from NPTII-positive $T_0$ plants are identified by ABI4 activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox™ bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for Abi4 activity using assays known in the art. After positive (i.e., for Abi4 expression) explants are identified, those shoots that fail to exhibit Abi4 activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for ABI4 expression are grafted to Pioneer hybrid 6440 in vitro-grown sunflower seedling rootstock. The rootstocks are prepared in the following manner. Seeds are dehulled and surface-sterilized for 20 minutes in a 20% Clorox™ bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with Parafilm™ film. After one week of culture on the medium, grafted plants are transferred to soil. In the first two weeks, they are maintained under high humidity conditions to acclimatize to a greenhouse environment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. An isolated nucleic acid molecule selected from the group consisting of: (a) a nucleic acid molecule comprising the sequence set forth in SEQ ID NO: 2; (b) a nucleic acid molecule comprising a sequence encoding the amino acid sequence set forth in SEQ ID NO: 3; (c) a nucleic acid molecule comprising a sequence having at least 98% sequence identity to the full length of the nucleotide sequence set forth in SEQ ID NO: 2, wherein nucleotides 124 through 291 encode amino acids 42 through 97 of SEQ ID NO: 3 and said nucleic acid molecule encodes a polypeptide having ABI4-like activity.

2. A nucleotide construct comprising a nucleic acid molecule of claim 1, wherein said nucleic acid molecule is operably linked to a promoter that drives expression in a plant cell.

3. A plant cell having stably incorporated into its genome at least one nucleotide construct comprising a nucleic acid molecule operably linked to a heterologous promoter that drives expression in said cell, wherein said nucleic acid molecule is selected from the group consisting of: (a) a nucleic acid molecule comprising the sequence set forth in SEQ ID NO: 2; (b) a nucleic acid molecule comprising a sequence encoding the amino acid sequence set forth in SEQ ID NO:3; (c) a nucleic acid molecule comprising a sequence having at least 98% sequence identity to the full length of the nucleotide sequence set forth in SEQ ID NO: 2, wherein nucleotides 124 through 291 encode amino acids 42 through 97 of SEQ ID NO: 3 and said nucleic acid molecule encodes a polypeptide having ABI4-like activity.

4. A transformed plant having stably incorporated into its genome at least one nucleotide construct comprising a nucleic acid molecule operably linked to a heterologous promoter that drives expression in a plant cell, wherein said nucleic acid molecule is selected from the group consisting of:
   a nucleic acid molecule comprising the sequence set forth in SEQ ID NO: 2;
   (b) a nucleic acid molecule comprising a sequence encoding the amino acid sequence set forth in SEQ ID NO: 3;
   (c) a nucleic acid molecule comprising a sequence having at least 98% sequence identity to the full length of the nucleotide sequence set forth in SEQ ID NO:2, wherein nucleotides 124 through 291 encode amino acids 42 through 97 of SEQ ID NO:3 and said nucleic acid molecule encodes a polypeptide having AB14-like activity.

5. The plant of claim 4, wherein said promoter is a constitutive promoter.

6. The plant of claim 4, wherein said promoter is a tissue-preferred promoter.

7. The plant of claim 4, wherein said promoter is an inducible promoter.

8. The plant of claim 7, wherein said promoter is a stress-inducible promoter.

9. The plant of claim 7, wherein said promoter is a pathogen-inducible promoter.

10. The plant of claim 4, wherein said plant is a monocot.

11. The plant of claim 10, wherein said monocot is maize, wheat, rice, barley, sorghum, or rye.

12. The plant of claim 4, wherein said plant is a dicot.

13. Transformed seed of the plant of claim 4.

14. A method for enhancing a plant stress response, said method comprising stably introducing into the genome of a plant at least one nucleotide construct comprising a nucleic acid molecule operably linked to a heterologous promoter that drives expression in a plant cell, wherein said nucleic acid molecule is selected from the group consisting of: (a) nucleic acid molecule comprising the sequence set forth in SEQ ID NO: 2; (b) a nucleic acid molecule comprising a sequence encoding the amino acid sequence set forth in SEQ ID NO: 3; (c) a nucleic acid molecule comprising a sequence having at least 98% sequence identity to the full length of the nucleotide sequence set forth in SEQ ID NO: 2, wherein nucleotides 124 through 291 encode amino acids 42 through 97 of SEQ ID NO: 3 and said nucleic acid molecule encodes a polypeptide having ABI4-like activity.

15. A method for improving plant stress tolerance, comprising transforming a plant with a construct to provide overexpression of SEQ ID NO: 2, thereby enabling the plant to respond to stress more rapidly or to a greater extent in relation to a isogenic untransformed plant.

16. A method for altering the composition or quantity of oil, starch, and/or protein in a plant seed, comprising stably incorporating into the genome of said plant at least one nucleotide construct comprising a nucleic acid molecule operably linked to a heterologous promoter that drives expression in a plant cell, wherein said nucleic acid molecule is selected from the group consisting of: (a) a nucleic acid molecule comprising the sequence set forth in SEQ ID NO: 2; (b) a nucleic acid molecule comprising a sequence encoding the amino acid sequence set forth in SEQ ID NO: 3; (c) a nucleic acid molecule comprising a sequence having at least 98% sequence identity to the full length of the nucleotide sequence set forth in SEQ ID NO: 2, wherein nucleotides 124 through 291 encode amino acids 42 through 97 of SEQ ID NO: 3 and said nucleic acid molecule encodes a polypeptide having ABI4-like activity.

17. A method for improving the yield of a plant, comprising stably incorporating into the genome of said plant at least one nucleotide construct comprising a nucleic acid molecule operably linked to a heterologous promoter that drives expression in a plant cell, wherein said nucleic acid molecule is selected from the group consisting of: (a) nucleic acid molecule comprising the sequence set forth in SEQ ID NO: 2; (b) a nucleic acid molecule comprising a sequence encoding the amino acid sequence set forth in SEQ ID NO: 3; (c) a nucleic acid molecule comprising a sequence having at least 98% sequence identity to the full length of the nucleotide sequences set forth in SEQ ID NO: 2, wherein nucleotides 124 through 291 encode amino acids 42 through 97 of SEQ ID NO: 3 and said nucleic acid molecule encodes a polypeptide having ABI4-like activity.

* * * * *

SEQUENCE LISTING

```
<160> NUMBER OF SEQ ID NOS: 5

<210> SEQ ID NO 1
<211> LENGTH: 2521
<212> TYPE: DNA
<213> ORGANISM: Zea mays
<220> FEATURE:
<221> NAME/KEY: promoter
<222> LOCATION: (1)...(2521)

<400> SEQUENCE: 1
ctgcaagcgt gcgggccacg tggcatgagg tttaagtggg ccaggcaaag gagaaatcag      60
cccatttgca cctctttcca tcccctttt ctattttcta ttttaatttc ctatttcaat     120
tctatgttcc aaatcaaatc tagttttaa tttcaaattc aagtttaatg cacaaacaat     180
aactccagca tgggatgcaa caaatttata tctatatata tttatattgt tgttaatcta     240
ttcattcaag taaatgcatc aaaatgcaca cacacaaaat atatgtattt taagaaagat     300
aatttctagt taagagaaca atttagaaat atatgatttg tcaaaggaat aactaaattc     360
ttatagagat catttttatt tacccttta ttagaaaaca ttattgtttt aggaaaagta     420
gttccaaagc taagacaatt cttatgggaa atatatttta attcaaaatc ttggagaatt     480
tcactaaact ttcaaaataa gatttttggg tgttacaaat gccccattga ctaggaggga     540
cttaagagtc caagagagat ctataggtca taagggcctc aagatccggt ctcctaacat     600
ggagggtgtg gcagagagag taggagagcc tcggtggcaa acatagtcct agtggtccta     660
ggagccctag gatctagtcc cctcgcatgg agagtggtgg agactaggtg agccctaggg     720
gcggagaggc cctcgggatt tggtctcctg aaatggaggg cctagactta gttggagtcg     780
agcatggtcc cctagggtgt ggagcccta gtcatatgac tagcatcgat tgaaccttt      840 tttgagtttt cttctatcaa atagatcttc cataggcata ttaccgatat ccaaagatat     900
gacatcctct tgacgtaaat agtagccatt acatatgttt gatctaactt gattgtatat     960
tattggcaaa acaatgtata agctctagta gctattcatt atttggccac actaagattt    1020
tgataaaaaa ataaaaaatt gtaaagttta gttacaacta gttaaattat gttcacatat    1080
cctcatgtct tctttacttt tcaatgtgcc cttgtcctcg tgttagggc gcatacacag      1140 ttattttgca tgcaacgata atatatatac agtttaaatg caacgcgcgt aacaaggtaa     1200
tattccacta gaatgtacat acgcgtttgc tagcgtatat gtatatatta taagatgatt     1260
tcaatggatt gtcacgacat ttcatgagtt aagtgtggtg ttcgtaaaga agacatatga    1320
```

-continued

```
tatgcaaggt gaaactttca taagtaaaag aaaatttcta atatttatgt tggtcaacct    1380
ttcgtatgtt taactaggtc gtttatggaa atatattataa cttttgtata tctcaaaata   1440
actttattat ggaaataaat tttaaaattg atgtaattat actgattata tacttaaata   1500
ttaatatctt tgtatatta atcaaagtta aaggaaatgg tacttagttt ttttttaaaaa   1560 aagcgaagga ttaatcgatt cgcgagaaca tttatatatg actgttgaca tgccaagcag   1620
gagggctttg cttctcacat ccgatgatat cactgggaaa tggagttgac cggtgcgtgc   1680
agtagtcatt tccaagaagc ttttaaccaa gttggtgaca ggtagacacg aaggaagccg   1740
cgtaggagta atcctagtac agtagtacta cgtagtaaaa atctgttgga cgatcgatcc   1800
aagtgaagca gtgcatcaaa gaacgctgca cacatcgatc tcgatcctgt ccctgcatgc   1860
atgcacgcac cgagcaacga agcgctgcac acaatgacac aagccagtaa gtcagaagtc   1920
gattgctcca tcaaccgtat actagcttaa ttccgcaatg actccgatga tctacatgct   1980
ggattccgca atgactccga tgatctacag catgcatggc acactccccc ggcctctacc   2040
acaccaacca acaagaatct ggcttttaa actaggtgag aaagattcaa acacacccgt    2100
ttttatacgt ttttgcaaaa ttctgaaaaa actagaaaac tgttgatagt aattttttgcc   2160 agtttctcat aatccaaaaa gaaacaaata aaatcattta ctgacacccg aatactgtat   2220
caattctggc tcggaatcta ctagatttta tagaaattac agacaaaaac tctcttttt    2280 taattccgaa actgatctaa agctgctcgc tgtactgcac tatgcactct ctcacctccc   2340
tttatatttg accaccgccc ctctccacca agcgcatcca cctcgacctc catccctagc   2400
gctctcgccc caaagcacgc cgcaggcgca gagccatcac caccatcctt ccccccctc     2460 tatctctctc taccccatcc ctcctctctc tcctcatata ccagcgacgc tgcctccttc    2520
c                                                                    2521
```

<210> SEQ ID NO 2
<211> LENGTH: 747
<212> TYPE: DNA
<213> ORGANISM: Zea mays
<220> FEATURE:
<221> NAME/KEY: CDS
<222> LOCATION: (1)...(747)

<400> SEQUENCE: 2

```
atg gaa gcc agc aac aat gag tcc gcg ccc acg gcc gag gca gct gca        48
Met Glu Ala Ser Asn Asn Glu Ser Ala Pro Thr Ala Glu Ala Ala Ala
1               5                   10                  15 ggc agc ggc ccg gcc ggc gga gaa ggg cgg aag ggc aag gcg ccc aag        96
Gly Ser Gly Pro Ala Gly Gly Glu Gly Arg Lys Gly Lys Ala Pro Lys
            20                  25                  30 ggc ggg ccc gag aac ggc aag ttc cgg tac cgc ggc gtg cgg cag cgg       144
Gly Gly Pro Glu Asn Gly Lys Phe Arg Tyr Arg Gly Val Arg Gln Arg
        35                  40                  45 agc tgg ggc aag tgg gtg gcg gag atc cgc gag ccg cgg aag cgc tcc       192
Ser Trp Gly Lys Trp Val Ala Glu Ile Arg Glu Pro Arg Lys Arg Ser
    50                  55                  60 cgc aag tgg ctc ggc acc ttc gcc acc gcc gag gac gcc gcg cgc gcc       240
Arg Lys Trp Leu Gly Thr Phe Ala Thr Ala Glu Asp Ala Ala Arg Ala
65                  70                  75                  80 tac gac cgc gcc gcg ctc ctc ctc tac ggc ccc cgc gcg cac ctc aac       288
Tyr Asp Arg Ala Ala Leu Leu Leu Tyr Gly Pro Arg Ala His Leu Asn
                85                  90                  95 ctc acc tcc ccg ccg cct cct acg ctc gcc gcg ccg cgc tcg cac ccg       336
```

```
Leu Thr Ser Pro Pro Pro Thr Leu Ala Ala Pro Arg Ser His Pro
            100                 105                 110 cac tcc tcc gcc acg tcg tct gcc ccg cca gcg ctc cgc ccg ctc ctg    384
His Ser Ser Ala Thr Ser Ser Ala Pro Pro Ala Leu Arg Pro Leu Leu
            115                 120                 125 ccg cgc ccg cca ctg cac cag ctc tcc agc gac ggt gct cct gca ccg    432
Pro Arg Pro Pro Leu His Gln Leu Ser Ser Asp Gly Ala Pro Ala Pro
    130                 135                 140 gat ttc cac tac cac aac cag ttc cag cgc cgt ctc ttg ccg cag ccg    480
Asp Phe His Tyr His Asn Gln Phe Gln Arg Arg Leu Leu Pro Gln Pro
145                 150                 155                 160 aca ccc aca cta tac tac gcc aac acg gcc acg gcg tcc aca gtg acc    528
Thr Pro Thr Leu Tyr Tyr Ala Asn Thr Ala Thr Ala Ser Thr Val Thr
                165                 170                 175 acc agt gtg ccg aca cgg gtg gcg gtt ccg cag gag ccg gcc atc gcg    576
Thr Ser Val Pro Thr Arg Val Ala Val Pro Gln Glu Pro Ala Ile Ala
            180                 185                 190 ccc gca gta ggc tcc tcg acg tca cta cag gag ccg cag gta ggt acg    624
Pro Ala Val Gly Ser Ser Thr Ser Leu Gln Glu Pro Gln Val Gly Thr
        195                 200                 205 ccg gag gag gcg cgc ggg gag gca ggg tgg gac tac aac ggc ggc gag    672
Pro Glu Glu Ala Arg Gly Glu Ala Gly Trp Asp Tyr Asn Gly Gly Glu
210                 215                 220 gag gag gat tat gcg gcg gcg ctg ctg tgg gac gag ccg gag ccc ttc    720
Glu Glu Asp Tyr Ala Ala Ala Leu Leu Trp Asp Glu Pro Glu Pro Phe
225                 230                 235                 240 ttc tgg ttt gat gtc ttc ctc aag tga                                747
Phe Trp Phe Asp Val Phe Leu Lys  *
                245
```

<210> SEQ ID NO 3
<211> LENGTH: 248
<212> TYPE: PRT
<213> ORGANISM: Zea mays

<400> SEQUENCE: 3

```
Met Glu Ala Ser Asn Asn Glu Ser Ala Pro Thr Ala Glu Ala Ala
1               5                   10                  15

Gly Ser Gly Pro Ala Gly Gly Glu Gly Arg Lys Gly Lys Ala Pro Lys
            20                  25                  30

Gly Gly Pro Glu Asn Gly Lys Phe Arg Tyr Arg Gly Val Arg Gln Arg
        35                  40                  45

Ser Trp Gly Lys Trp Val Ala Glu Ile Arg Glu Pro Arg Lys Arg Ser
    50                  55                  60

Arg Lys Trp Leu Gly Thr Phe Ala Thr Ala Glu Asp Ala Ala Arg Ala
65                  70                  75                  80

Tyr Asp Arg Ala Ala Leu Leu Leu Tyr Gly Pro Arg Ala His Leu Asn
                85                  90                  95

Leu Thr Ser Pro Pro Pro Thr Leu Ala Ala Pro Arg Ser His Pro
            100                 105                 110

His Ser Ser Ala Thr Ser Ser Ala Pro Pro Ala Leu Arg Pro Leu Leu
            115                 120                 125

Pro Arg Pro Pro Leu His Gln Leu Ser Ser Asp Gly Ala Pro Ala Pro
    130                 135                 140

Asp Phe His Tyr His Asn Gln Phe Gln Arg Arg Leu Leu Pro Gln Pro
145                 150                 155                 160

Thr Pro Thr Leu Tyr Tyr Ala Asn Thr Ala Thr Ala Ser Thr Val Thr
                165                 170                 175
```

```
Thr Ser Val Pro Thr Arg Val Ala Val Pro Gln Glu Pro Ala Ile Ala
            180                 185                 190

Pro Ala Val Gly Ser Ser Thr Ser Leu Gln Glu Pro Gln Val Gly Thr
        195                 200                 205

Pro Glu Glu Ala Arg Gly Glu Ala Gly Trp Asp Tyr Asn Gly Gly Glu
    210                 215                 220

Glu Glu Asp Tyr Ala Ala Ala Leu Leu Trp Asp Glu Pro Glu Pro Phe
225                 230                 235                 240

Phe Trp Phe Asp Val Phe Leu Lys
                245

<210> SEQ ID NO 4
<211> LENGTH: 1145
<212> TYPE: DNA
<213> ORGANISM: Zea mays
<220> FEATURE:
<221> NAME/KEY: CDS
<222> LOCATION: (1)...(747)

<400> SEQUENCE: 4 atg gaa gcc agc aac aat gag tcc gcg ccc acg gcc gag gca gct gca      48
Met Glu Ala Ser Asn Asn Glu Ser Ala Pro Thr Ala Glu Ala Ala Ala
 1               5                  10                  15 ggc agc ggc ccg gcc ggc gga gaa ggg cgg aag ggc aag gcg ccc aag      96
Gly Ser Gly Pro Ala Gly Gly Glu Gly Arg Lys Gly Lys Ala Pro Lys
            20                  25                  30 ggc ggg ccc gag aac ggc aag ttc cgg tac cgc ggc gtg cgg cag cgg     144
Gly Gly Pro Glu Asn Gly Lys Phe Arg Tyr Arg Gly Val Arg Gln Arg
        35                  40                  45 agc tgg ggc aag tgg gtg gcg gag atc cgc gag ccg cgg aag cgc tcc     192
Ser Trp Gly Lys Trp Val Ala Glu Ile Arg Glu Pro Arg Lys Arg Ser
    50                  55                  60 cgc aag tgg ctc ggc acc ttc gcc acc gcc gag gac gcc gcg cgc gcc     240
Arg Lys Trp Leu Gly Thr Phe Ala Thr Ala Glu Asp Ala Ala Arg Ala
65                  70                  75                  80 tac gac cgc gcc gcg ctc ctc ctc tac ggc ccc cgc gcg cac ctc aac     288
Tyr Asp Arg Ala Ala Leu Leu Leu Tyr Gly Pro Arg Ala His Leu Asn
                85                  90                  95 ctc acc tcc ccg ccg cct cct acg ctc gcc gcg ccg cgc tcg cac ccg     336
Leu Thr Ser Pro Pro Pro Pro Thr Leu Ala Ala Pro Arg Ser His Pro
            100                 105                 110 cac tcc tcc gcc acg tcg tct gcc ccg cca gcg ctc cgc ccg ctc ctg     384
His Ser Ser Ala Thr Ser Ser Ala Pro Pro Ala Leu Arg Pro Leu Leu
        115                 120                 125 ccg cgc ccg cca ctg cac cag ctc tcc agc gac ggt gct cct gca ccg     432
Pro Arg Pro Pro Leu His Gln Leu Ser Ser Asp Gly Ala Pro Ala Pro
    130                 135                 140 gat ttc cac tac cac aac cag ttc cag cgc cgt ctc ttg ccg cag ccg     480
Asp Phe His Tyr His Asn Gln Phe Gln Arg Arg Leu Leu Pro Gln Pro
145                 150                 155                 160 aca ccc aca cta tac tac gcc aac acg gcc acg gcg tcc aca gtg acc     528
Thr Pro Thr Leu Tyr Tyr Ala Asn Thr Ala Thr Ala Ser Thr Val Thr
                165                 170                 175 acc agt gtg ccg aca cgg gtg gcg gtt ccg cag gag ccg gcc atc gcg     576
Thr Ser Val Pro Thr Arg Val Ala Val Pro Gln Glu Pro Ala Ile Ala
            180                 185                 190 ccc gca gta ggc tcc tcg acg tca cta cag gag ccg cag gta ggt acg     624
Pro Ala Val Gly Ser Ser Thr Ser Leu Gln Glu Pro Gln Val Gly Thr
        195                 200                 205
```

| | | | | | | | | | | | | | | |
|---|---|---|---|---|---|---|---|---|---|---|---|---|---|---|
| ccg | gag | gag | gcg | cgc | ggg | gag | gca | ggg | tgg | gac | tac | aac | ggc | ggc | gag | 672 |
| Pro | Glu | Glu | Ala | Arg | Gly | Glu | Ala | Gly | Trp | Asp | Tyr | Asn | Gly | Gly | Glu |
| | 210 | | | | 215 | | | | | 220 | | | | | |

| | | | | | | | | | | | | | | | |
|---|---|---|---|---|---|---|---|---|---|---|---|---|---|---|---|
| gag | gag | gat | tat | gcg | gcg | gcg | ctg | ctg | tgg | gac | gag | ccg | gag | ccc | ttc | 720 |
| Glu | Glu | Asp | Tyr | Ala | Ala | Ala | Leu | Leu | Trp | Asp | Glu | Pro | Glu | Pro | Phe |
| 225 | | | | 230 | | | | | 235 | | | | | 240 | |

| | | | | | | | | | | | |
|---|---|---|---|---|---|---|---|---|---|---|---|
| ttc | tgg | ttt | gat | gtc | ttc | ctc | aag | tga | tggccagcgc | acgacgctgc | | 767 |
| Phe | Trp | Phe | Asp | Val | Phe | Leu | Lys | * | | |
| | | | | 245 | | | | | | |

```
atgccaactc gaatcctgca tggttggttt ggagtttcgg agtgacggca gctcatgctc        827
atgcatctgc atgcatgtgt tgggcaagta agcaagcaag aaaggtagat aggcttgcta        887
gctagggttt ctgattcctt tgtactaaat tatctttata ttttttttat cttatccttc        947
ttttttccct aagggtgtga ttgagtata gtaatgttag gtggtattac tggtgggagg        1007
atttagggtt ctttgttgat ttaaagattc aattttgaat cacatcgaat cgatttcttg        1067
catggggatg caatctattt aattgtggca tgtataaaaa tcagcgatgc aacaaaaaaa        1127
aaaaaaaaaa aaaaaaaa                                                     1145

<210> SEQ ID NO 5
<211> LENGTH: 3666
<212> TYPE: DNA
<213> ORGANISM: Zea mays
<220> FEATURE:
<221> NAME/KEY: CDS
<222> LOCATION: (2522)...(3268)

<400> SEQUENCE: 5
ctgcaagcgt gcgggccacg tggcatgagg tttaagtggg ccaggcaaag gagaaatcag         60
cccatttgca cctctttcca tccccttttt ctattttcta tttaatttc ctatttcaat        120
tctatgttcc aaatcaaatc tagttttaa tttcaaattc aagtttaatg cacaaacaat        180
aactccagca tgggatgcaa caaatttata tctatatata tttatattgt tgttaatcta        240
ttcattcaag taaatgcatc aaaatgcaca cacacaaaat atatgtattt taagaaagat        300
aatttctagt taagagaaca atttagaaat atatgatttg tcaaaggaat aactaaattc        360
ttatagagat cattttatt taccctttta ttagaaaaca ttattgtttt aggaaaagta        420
gttccaaagc taagacaatt cttatgggaa atatatttta attcaaaatc ttggagaatt        480
tcactaaact ttcaaaataa gattttgggg tgttacaaat gccccattga ctaggaggga        540
cttaagagtc caagagagat ctataggtca taagggcctc aagatccggt ctcctaacat        600
ggagggtgtg gcagagagag taggagagcc tcggtggcaa acatagtcct agtggtccta        660
ggagccctag gatctagtcc cctcgcatgg agagtggtgg agactaggtg agccctaggg        720
gcggagaggc cctcgggatt tggtctcctg aaatggaggg cctagactta gttggagtcg        780
agcatggtcc cctagggtgt ggagccccta gtcatatgac tagcatcgat tgaacctttt        840
tttgagtttt cttctatcaa atagatcttc cataggcata ttaccgatat ccaaagatat        900
gacatcctct tgacgtaaat agtagccatt acatatgttt gatctaactt gattgtatat        960
tattggcaaa acaatgtata agctctagta gctattcatt atttggccac actaagattt        1020
tgataaaaaa ataaaaaatt gtaaagttta gttacaacta gttaaattat gttcacatat        1080
cctcatgtct tctttacttt tcaatgtgcc cttgtcctcg tgttaggggc gcatacacag        1140
ttattttgca tgcaacgata atatatatac agtttaaatg caacgcgcgt aacaaggtaa        1200
tattccacta gaatgtacat acgcgtttgc tagcgtatat gtatatatta taagatgatt        1260
```

```
tcaatggatt gtcacgacat ttcatgagtt aagtgtggtg ttcgtaaaga agacatatga   1320
tatgcaaggt gaaactttca taagtaaaag aaaatttcta atatttatgt tggtcaacct   1380
ttcgtatgtt taactaggtc gtttatggaa aatattataa cttttgtata tctcaaaata   1440
actttattat ggaaataaat tttaaaattg atgtaattat actgattata tacttaaata   1500
ttaatatctt tgtatattta atcaaagtta aaggaaatgg tacttagttt ttttttaaaaa   1560 aagcgaagga ttaatcgatt cgcgagaaca tttatatatg actgttgaca tgccaagcag   1620
gagggctttg cttctcacat ccgatgatat cactgggaaa tggagttgac cggtgcgtgc   1680
agtagtcatt tccaagaagc ttttaaccaa gttggtgaca ggtagacacg aaggaagccg   1740
cgtaggagta atcctagtac agtagtacta cgtagtaaaa atctgttgga cgatcgatcc   1800
aagtgaagca gtgcatcaaa gaacgctgca cacatcgatc tcgatcctgt ccctgcatgc   1860
atgcacgcac cgagcaacga agcgctgcac acaatgacac aagccagtaa gtcagaagtc   1920
gattgctcca tcaaccgtat actagcttaa ttccgcaatg actccgatga tctacatgct   1980
ggattccgca atgactccga tgatctacag catgcatggc acactccccc ggcctctacc   2040
acaccaacca acaagaatct ggcttttta actaggtgag aaagattcaa acacacccgt   2100
ttttatacgt ttttgcaaaa ttctgaaaaa actagaaaac tgttgatagt aatttttgcc   2160
agtttctcat aatccaaaaa gaaacaaata aaatcattta ctgacacccg aatactgtat   2220
caattctggc tcggaatcta ctagatttta tagaaattac agacaaaaac tctcttttt   2280 taattccgaa actgatctaa agctgctcgc tgtactgcac tatgcactct ctcacctccc   2340
tttatatttg accaccgccc ctctccacca agcgcatcca cctcgacctc catccctagc   2400
gctctcgccc caaagcacgc cgcaggcgca gagccatcac caccatcctt cccccccctc   2460
tatctctctc taccccatcc ctcctctctc tcctcatata ccagcgacgc tgcctccttc   2520 c atg gaa gcc agc aac aat gag tcc gcg ccc acg gcc gag gca gct gca   2569
         Met Glu Ala Ser Asn Asn Glu Ser Ala Pro Thr Ala Glu Ala Ala
           1               5                  10                  15 ggc agc ggc ccg gcc ggc gga gaa ggg cgg aag ggc aag gcg ccc aag   2617
Gly Ser Gly Pro Ala Gly Gly Glu Gly Arg Lys Gly Lys Ala Pro Lys
             20                  25                  30 ggc ggg ccc gag aac ggc aag ttc cgg tac cgc ggc gtg cgg cag cgg   2665
Gly Gly Pro Glu Asn Gly Lys Phe Arg Tyr Arg Gly Val Arg Gln Arg
         35                  40                  45 agc tgg ggc aag tgg gtg gcg gag atc cgc gag ccg cgg aag cgc tcc   2713
Ser Trp Gly Lys Trp Val Ala Glu Ile Arg Glu Pro Arg Lys Arg Ser
     50                  55                  60 cgc aag tgg ctc ggc acc ttc gcc acc gcc gag gac gcc gcg cgc gcc   2761
Arg Lys Trp Leu Gly Thr Phe Ala Thr Ala Glu Asp Ala Ala Arg Ala
 65                  70                  75                  80 tac gac cgc gcc gcg ctc ctc ctc tac ggc ccc cgc gcg cac ctc aac   2809
Tyr Asp Arg Ala Ala Leu Leu Leu Tyr Gly Pro Arg Ala His Leu Asn
                 85                  90                  95 ctc acc tcc ccg ccg cct cct acg ctc gcc gcg ccg cgc tcg cac ccg   2857
Leu Thr Ser Pro Pro Pro Pro Thr Leu Ala Ala Pro Arg Ser His Pro
            100                 105                 110 cac tcc tcc gcc acg tcg tct gcc ccg cca gcg ctc cgc ccg ctc ctg   2905
His Ser Ser Ala Thr Ser Ser Ala Pro Pro Ala Leu Arg Pro Leu Leu
        115                 120                 125 ccg cgc ccg cca ctg cac cag ctc tcc agc gac ggt gct cct gca ccg   2953
Pro Arg Pro Pro Leu His Gln Leu Ser Ser Asp Gly Ala Pro Ala Pro
    130                 135                 140 gat ttc cac tac cac aac cag ttc cag cgc cgt ctc ttg ccg cag ccg   3001
```

-continued

```
Asp Phe His Tyr His Asn Gln Phe Gln Arg Arg Leu Leu Pro Gln Pro
145                 150                 155                 160 aca ccc aca cta tac tac gcc aac acg gcc acg gcg tcc aca gtg acc      3049
Thr Pro Thr Leu Tyr Tyr Ala Asn Thr Ala Thr Ala Ser Thr Val Thr
            165                 170                 175 acc agt gtg ccg aca cgg gtg gcg gtt ccg cag gag ccg gcc atc gcg      3097
Thr Ser Val Pro Thr Arg Val Ala Val Pro Gln Glu Pro Ala Ile Ala
            180                 185                 190 ccc gca gta ggc tcc tcg acg tca cta cag gag ccg cag gta ggt acg      3145
Pro Ala Val Gly Ser Ser Thr Ser Leu Gln Glu Pro Gln Val Gly Thr
            195                 200                 205 ccg gag gag gcg cgc ggg gag gca ggg tgg gac tac aac ggc ggc gag      3193
Pro Glu Glu Ala Arg Gly Glu Ala Gly Trp Asp Tyr Asn Gly Gly Glu
    210                 215                 220 gag gag gat tat gcg gcg gcg ctg ctg tgg gac gag ccg gag ccc ttc      3241
Glu Glu Asp Tyr Ala Ala Ala Leu Leu Trp Asp Glu Pro Glu Pro Phe
225                 230                 235                 240 ttc tgg ttt gat gtc ttc ctc aag tga tggccagcgc acgacgctgc            3288
Phe Trp Phe Asp Val Phe Leu Lys *
                245 atgccaactc gaatcctgca tggttggttt ggagtttcgg agtgacggca gctcatgctc    3348 atgcatctgc atgcatgtgt tgggcaagta agcaagcaag aaaggtagat aggcttgcta    3408 gctagggttt ctgattcctt tgtactaaat tatctttata tttttttttat cttatccttc   3468 ttttttccct aagggtgtga ttgaggtata gtaatgttag gtggtattac tggtgggagg    3528 atttagggtt ctttgttgat ttaaagattc aattttgaat cacatcgaat cgatttcttg    3588 catggggatg caatctattt aattgtggca tgtataaaaa tcagcgatgc aacaaaaaaa    3648 aaaaaaaaaa aaaaaaaa                                                   3666
```